US010227569B2

(12) United States Patent
Moore et al.

(10) Patent No.: US 10,227,569 B2
(45) Date of Patent: Mar. 12, 2019

(54) RESPIRATORY SYNCYTIAL VIRUS EXPRESSION VECTORS

(75) Inventors: Martin L. Moore, Decatur, GA (US); Anne Hotard, Atlanta, GA (US)

(73) Assignees: EMORY UNIVERSITY, Atlanta, GA (US); CHILDREN'S HEALTHCARE OF ATLANTA, INC., Atlanta, GA (US)

( * ) Notice: Subject to any disclaimer, the term of this patent is extended or adjusted under 35 U.S.C. 154(b) by 0 days.

(21) Appl. No.: 13/444,338

(22) Filed: Apr. 11, 2012

(65) Prior Publication Data

US 2012/0264217 A1 Oct. 18, 2012

Related U.S. Application Data

(60) Provisional application No. 61/474,365, filed on Apr. 12, 2011.

(51) Int. Cl.

| | |
|---|---|
| ***A61K 39/215*** | (2006.01) |
| ***A61K 39/225*** | (2006.01) |
| ***C07H 21/04*** | (2006.01) |
| ***C12N 15/00*** | (2006.01) |
| ***C12N 7/00*** | (2006.01) |
| ***C12N 15/86*** | (2006.01) |

(52) U.S. Cl.

CPC ............... *C12N 7/00* (2013.01); *C12N 15/86* (2013.01); *C12N 2760/18543* (2013.01); *C12N 2760/18552* (2013.01); *C12N 2800/204* (2013.01); *C12N 2800/50* (2013.01)

(58) Field of Classification Search

CPC ...... A61K 2039/525; A61K 2039/5256; A61K 2039/53; A61K 2039/541; A61K 39/12

USPC .......................................................... 435/320

See application file for complete search history.

(56) References Cited

U.S. PATENT DOCUMENTS

| | | | | |
|---|---|---|---|---|
| 5,618,682 | A | 4/1997 | Scheirer | |
| 5,674,713 | A | 10/1997 | McElroy et al. | |
| 5,976,796 | A | 11/1999 | Szalay et al. | |
| 6,074,859 | A | 6/2000 | Hirokawa et al. | |
| 6,790,449 | B2 | 9/2004 | Collins | |
| 7,572,904 | B2 * | 8/2009 | Cheng et al. | 536/23.72 |
| 7,892,822 | B1 | 2/2011 | Koszinowski et al. | |

OTHER PUBLICATIONS

Shizuya et al., Cloning and stable maintenance of 300-kilobase-pair fragments of human DNA in *Escherichia coli* using an F-factor-based vector, 1992, Proc. Natl. Acad. Sci. USA, 89:8794-8797.*

The Wellcome Trust Sanger Institute, Functional Genomics, 2002, The Wellcome Trust Sanger Inst. Hinxton, Cambridge, pp. 1-114.*

Adler, et al., (2003), "Cloning of herpesviral genomes as bacterial artificial chromosomes.", Reviews in Medical Virology, 13(2): 111-121.

Buchholz, et al., (2000), "Chimeric Bovine Respiratory Syncytial Virus with Glycoprotein Gene Substitutions from Human Respiratory Syncytial Virus (HRSV): Effects on Host Range and Evaluation as a Live-Attenuated HRSV Vaccine.", Journal of Virology, 74(3): 1187-1199.

Clements, et al., (1991), "Evaluation of bovine, cold-adapted human, and wild-type human parainfluenza type 3 viruses in adult volunteers and in chimpanzees.", Journal of Clinical Microbiology, 29(6): 1175-1182.

Collins, et al., (1986), "Nucleotide sequences for the gene junctions of human respiratory syncytial virus reveal distinctive features of intergenic structure and gene order.", Proceedings of the National Academy of Sciences, 83(13): 4594-4598.

Collins, et al., (1987), "Gene overlap and site-specific attenuation of transcription of the viral polymerase L gene of human respiratory syncytial virus.", Proceedings of the National Academy of Sciences, 84(15): 5134-5138.

Collins, et al., (1995), "Production of infectious human respiratory syncytial virus from cloned cDNA confirms an essential role for the transcription elongation factor from the 5' proximal open reading frame of the M2 mRNA in gene expression and provides a capability for vaccine development.", Proceedings of the National Academy of Sciences, 92(25): 11563-11567.

Cunningham, et al., (1993), "Lentivirus envelope sequences and pro viral genomes are stabilized in *Escherichia coli* when cloned in low-copy-number plasmid vectors.", Gene, 124(1): 93-98.

De Wet, et al., (1987), "Firefly luciferase gene: structure and expression in mammalian cells.", Molecular and Cellular Biology, 7(2): 725-737.

Karron, et al., (2005), "Identification of a Recombinant Live Attenuated Respiratory Syncytial Virus Vaccine Candidate That Is Highly Attenuated in Infants.", Journal of Infectious Diseases, 191(7): 1093-1104.

Mallipeddi, et al., (1992), "Sequence comparison between the phosphoprotein mRNAs of human and bovine respiratory syncytial viruses identifies a divergent domain in the predicted protein.", Journal of General Virology, 73(Pt 9): 2441-2444.

Mallipeddi, et al., (1993), "Sequence variability of the glycoprotein gene of bovine respiratory syncytial virus.", Journal of General Virology, 74(9): 2001-2004.

Maniatis, et al., (1987), "Regulation of inducible and tissue-specific gene expression.", Science, 236(4806): 1237-1245.

Merzlyak, et al., (2007), "Bright monomeric red fluorescent protein with an extended fluorescence lifetime.", Nature Methods, 4(7): 555-557.

(Continued)

*Primary Examiner* — Barry A Chestnut

(74) *Attorney, Agent, or Firm* — Emory Patent Group

(57) ABSTRACT

In certain embodiments, the disclosure relates to vectors containing bacterial nucleic acid sequences and a paramyxovirus gene. Typically, the expression vector comprises a bacterial artificial chromosome (BAC), and a nucleic acid sequence comprising a respiratory syncytial virus (RSV) gene in operable combination with a regulatory element and optionally a reporter gene.

10 Claims, 5 Drawing Sheets

Figure 1:
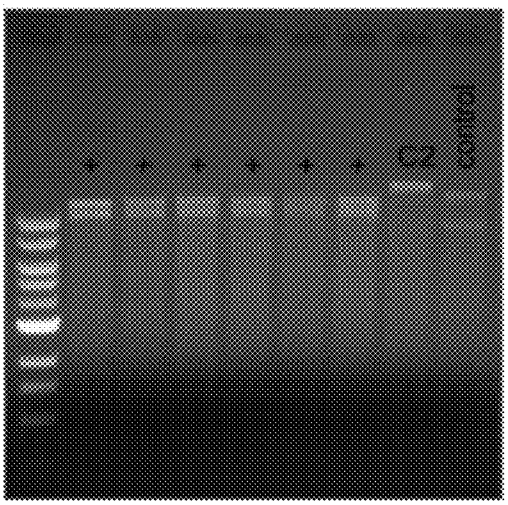

Specification includes a Sequence Listing.

(56) References Cited

OTHER PUBLICATIONS

Needleman, et al., (1970), "A general method applicable to the search for similarities in the amino acid sequence of two proteins.", Journal of Molecular Biology, 48(3): 443-453.

Pastey, et al., (1993), "Structure and sequence comparison of bovine respiratory syncytial virus fusion protein.", Virus Research, 29(2): 195-202.

Pastey, et al., (1995), "Nucleotide sequence analysis of the non-structural NS1 (1C) and NS2 (1B) protein genes of bovine respiratory syncytial virus.", Journal of General Virology, 76(1): 193-197.

Pearson, et al., (1988), "Improved tools for biological sequence comparison.", Proceedings of the National Academy of Sciences, 85(8): 2444-2448.

Randhawa, et al., (1995), "Nucleotide Sequences of the Genes Encoding the Putative Attachment Glycoprotein (G) of Mouse and Tissue Culture-Passaged Strains of Pneumonia Virus of Mice.", Virology, 207(1): 240-245.

Roth, et al., (2011), "Recovery of infectious virus from full-length cowpox virus (CPXV) DNA cloned as a bacterial artificial chromosome (BAC).", Veterinary Research, 42(1): 3.

Shcherbo, et al., (2009), "Far-red fluorescent tags for protein imaging in living tissues." Biochemical Journal, 418(3): 567-574.

Shizuya, et al., (1992), "Cloning and stable maintenance of 300-kilobase-pair fragments of human DNA in *Escherichia coli* using an F-factor-based vector.", Proceedings of the National Academy of Sciences, 89(18): 8794-8797.

Shizuya, et al., (2001), "The development and applications of the bacterial artificial chromosome cloning system.", The Keio Journal of Medicine, 50(1): 26-30.

Skiadopoulos, et al., (2006), "Individual contributions of the human metapneumovirus F, G, and SH surface glycoproteins to the induction of neutralizing antibodies and protective immunity.", Virology, 345(2): 492-501.

Smith, et al., (1981), "Comparison of biosequences.", Advances in Applied Mathematics, 2(4): 482-489.

Voss, et al., (1986), "The role of enhancers in the regulation of cell-type-specific transcriptional control.", Trends in Biochemical Sciences, 11(7): 287-289.

Warming, et al., (2005), "Simple and highly efficient BAC recombineering using galK selection.", Nucleic Acids Research, 33(4): e36.

Zamora, et al., (1992), "Sequence analysis of M2 mRNA of bovine respiratory syncytial virus obtained from an F-M2 dicistronic mRNA suggests structural homology with that of human respiratory syncytial virus.", Journal of General Virology, 73(3): 737-741.

Zamora, et al., (1992), "Gene junction sequences of bovine respiratory syncytial virus.", Virus Research, 24(1): 115-121.

* cited by examiner

RESPIRATORY SYNCYTIAL VIRUS EXPRESSION VECTORS

CROSS REFERENCE TO RELATED APPLICATIONS

This application claims priority to U.S. Provisional Application No. 61/474,365 filed Apr. 12, 2011, hereby incorporated by reference in its entirety.

This invention was made with government support under Grant No UL1RR025008 awarded by the National Institutes of Health. The government has certain rights in the invention.

BACKGROUND

Human respiratory syncytial virus (RSV) causes respiratory tract infections. It is the major cause of hospital visits during infancy and childhood. After translation of viral mRNAs, a full-length (+) antigenomic RNA is produced as a template for replication of the (−) RNA genome. Infectious recombinant RSV (rRSV) particles may be recovered from transfected plasmids. Co-expression of RSV N, P, L, and M2-1 proteins as well as the full-length antigenomic RNA is sufficient for RSV replication. See Collins et al., Proc Natl Acad Sci USA., 1995, 92(25):11563-11567 and U.S. Pat. No. 6,790,449.

Despite the existence of methods of generating RSV particles from cloned cDNA, stability of RSV cDNA remains a challenge. A region of the RSV small hydrophobic protein (SH) gene is unstable as cloned cDNA. See e.g., Skiadopoulos et al., Virology 345, 492-501 (2006). Investigators have suffered failures in cloning RSV cDNA in plasmids, despite extensive experience with other viruses and cDNA cloning. Labs typically use a RSV antigenomic cDNA cloned in the plasmid pBR322. In order to maintain the antigenomic cDNA in this plasmid, one typically grows the bacteria at 30° C. and low aeration. Nevertheless, plasmids frequently undergo rearrangements and clone loss. Taken together, plasmid stability is a factor limiting progress in RSV research and vaccine development. Thus, there is a need to identify improved methods of generating RSV.

One may recover viruses from bacterial artificial chromosome (BAC) vectors. See Roth et al., Vet Res., 2011, 42(1):3 and Alder et al., Rev Med. Virol., 2003, 13(2):111-21 and U.S. Pat. No. 7,892,822. BAC recombineering refers to a method of introducing mutations in cDNAs cloned in a BAC vectors via homologous recombination in *E coli*. A BAC recombineering system based on selection and counter-selection of the galK operon was disclosed by Warming et al, Nucleic Acids Research, 2005, 33, e36. References cited herein are not an admission of prior art.

SUMMARY

In certain embodiments, the disclosure relates to vectors comprising a bacterial artificial chromosome (BAC), and a nucleic acid sequence comprising a paramyxovirus genome, antigenome, or gene of a paramyxovirus. Typically, the paramyxovirus is respiratory syncytial virus (RSV), human metapneumovirus, nipah virus, hendra virus, or pneumonia virus and the BAC contains all genes that are essential for the generation of an infectious viral particle in a host cell. The nucleic acid sequence may be a viral genome or antigenome in operable combination with a regulatory element. Typically, the bacterial artificial chromosome comprises one or more genes selected from the group consisting of oriS, repE, parA, and parB genes of Factor F in operable combination with a selectable marker, e.g., a gene that provides resistance to an antibiotic.

The nucleic acid sequence may be the genomic or antigenomic sequence of the virus which is optionally mutated, e.g., RSV strain which is optionally mutated. In certain embodiments, the expression vector is a plasmid comprising MluI, ClaI, BstBI, SacI restriction endonuclease cleavage sites and optionally an AvrII restriction endonuclease cleavage site outside the region of the wild-type viral sequence or outside the sequences that encode viral genes or outside the viral genome or antigenome. In certain embodiments, the nucleic acid sequence further comprises a selectable marker or reporter gene in operable combination therewith, e.g., a gene that encodes a fluorescent protein.

In certain embodiments, the disclosure relates to isolated bacteria comprising one or more vectors disclosed herein, and other embodiments, the disclosure relates to an isolated cell comprising one or more vectors disclosed herein. In certain embodiments, the vector comprises an RSV antigenome and one or more vectors selected from the group consisting of: a vector encoding an N protein of RSV, a vector encoding a P protein of RSV, a vector encoding an L protein of RSV, and a vector encoding an M2-1 protein of RSV. Typically, the vector comprises a regulatory element, e.g., promoter, and the isolated eukaryotic cell expresses a nucleic acid or polypeptide that activates the regulatory element, e.g., encodes a polypeptide that activates transcription downstream of the promoter. In certain embodiments, the promoter is T7, and the polypeptide that activates transcription downstream of the promoter is T7 RNA polymerase.

In certain embodiments, the disclosure relates to methods of generating respiratory syncytial virus (RSV) particles comprising inserting a vector with a BAC gene and a RSV antigenome into an isolated eukaryotic cell and inserting one or more vectors selected from the group consisting of: a vector encoding an N protein of RSV, a vector encoding a P protein of RSV, a vector encoding an L protein of RSV, and a vector encoding an M2-1 protein of RSV into the cell under conditions such that RSV particle is formed. Inserting a vector into a cell may occur by physically injecting, electroporating, or mixing the cell and the vector under conditions such that the vector infects the cell.

In certain embodiments, the disclosure relates to a non-naturally occurring isolated nucleic acid comprising or consisting essential of SEQ ID NO: 1, SEQ ID NO: 2, or SEQ ID NO: 3 or a sequence with substantial identity.

In certain embodiments, the disclosure relates to a non-naturally occurring isolated nucleic acid comprising or consisting essential of SEQ ID NO: 4 and SEQ ID NO: 5 or a sequence with substantial identity.

In certain embodiments, the disclosure relates to a recombinant vector comprising a bacterial artificial chromosome, a nucleic acid sequence comprising SEQ ID NO: 4 or a sequence with substantial identity; and a nucleic acid sequence comprising SEQ ID NO: 5 or a sequence with substantial identity.

In certain embodiment, the disclosure relates to processes of producing a recombinant vector comprising a bacterial artificial chromosome and SacI, ClaI and AvrII restriction endonuclease cleavage sites comprising mixing a nucleic acid comprising a bacterial artificial chromosome and a nucleic acid comprising SacI, ClaI and AvrII restriction endonuclease cleavage sites under conditions such that a continuous nucleic acid comprising a bacterial artificial chromosome and a SacI, ClaI and AvrII restriction endonuclease cleavage sites is formed.

In certain embodiments, the disclosure relates to a recombinant vector comprising SEQ ID NO: 6 or a sequence with substantial identity.

BRIEF DESCRIPTIONS OF THE FIGURES

FIG. 1 shows a gel after insertion of galK operon into BAC-RSV by recombineering. MluI digest. Lane 1, ladder marker. Mini-prep BAC DNAs (lanes 2 to 7). Lane 8, parental BAC-RSV “C2” clone. Lane 9, galK-containing plasmid. galK operon has a Mlu I restriction site that serves as a marker for introduction of galK by homologous recombination.

Figure 2:
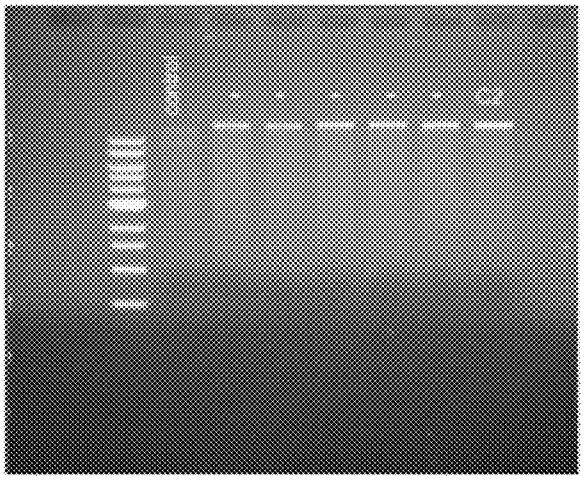
Figure 3A:
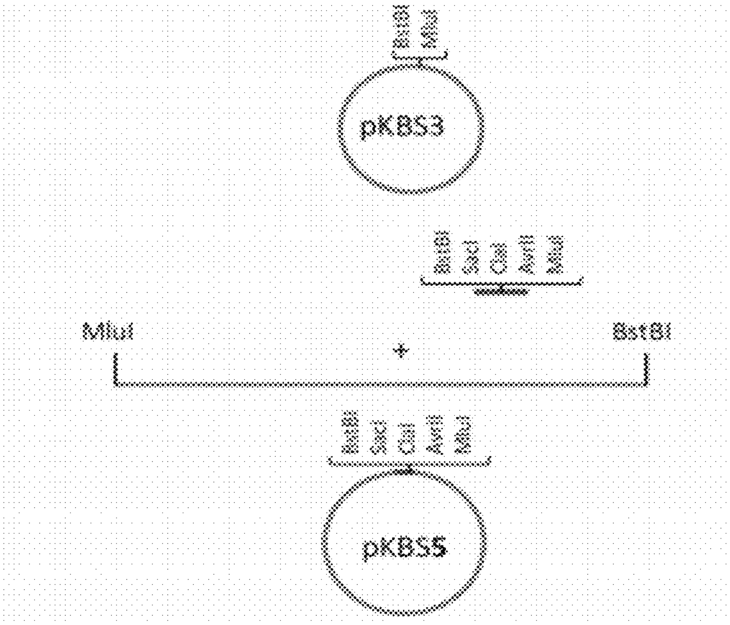
Figure 3B:
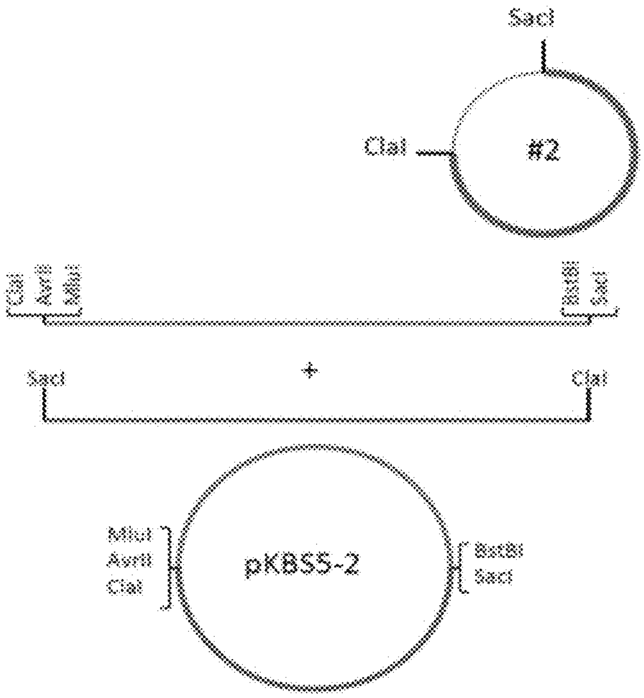
Figure 3C:
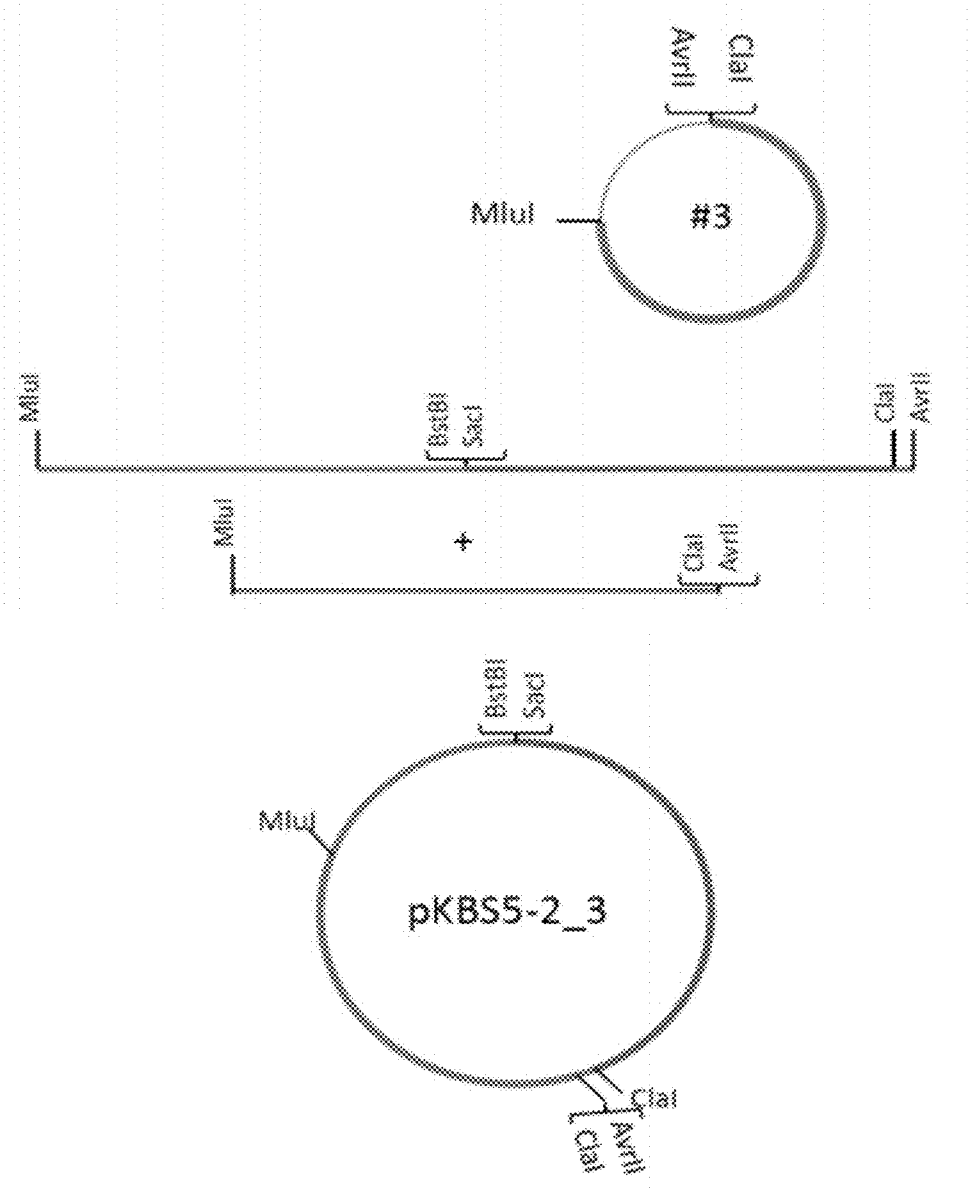
Figure 3D:
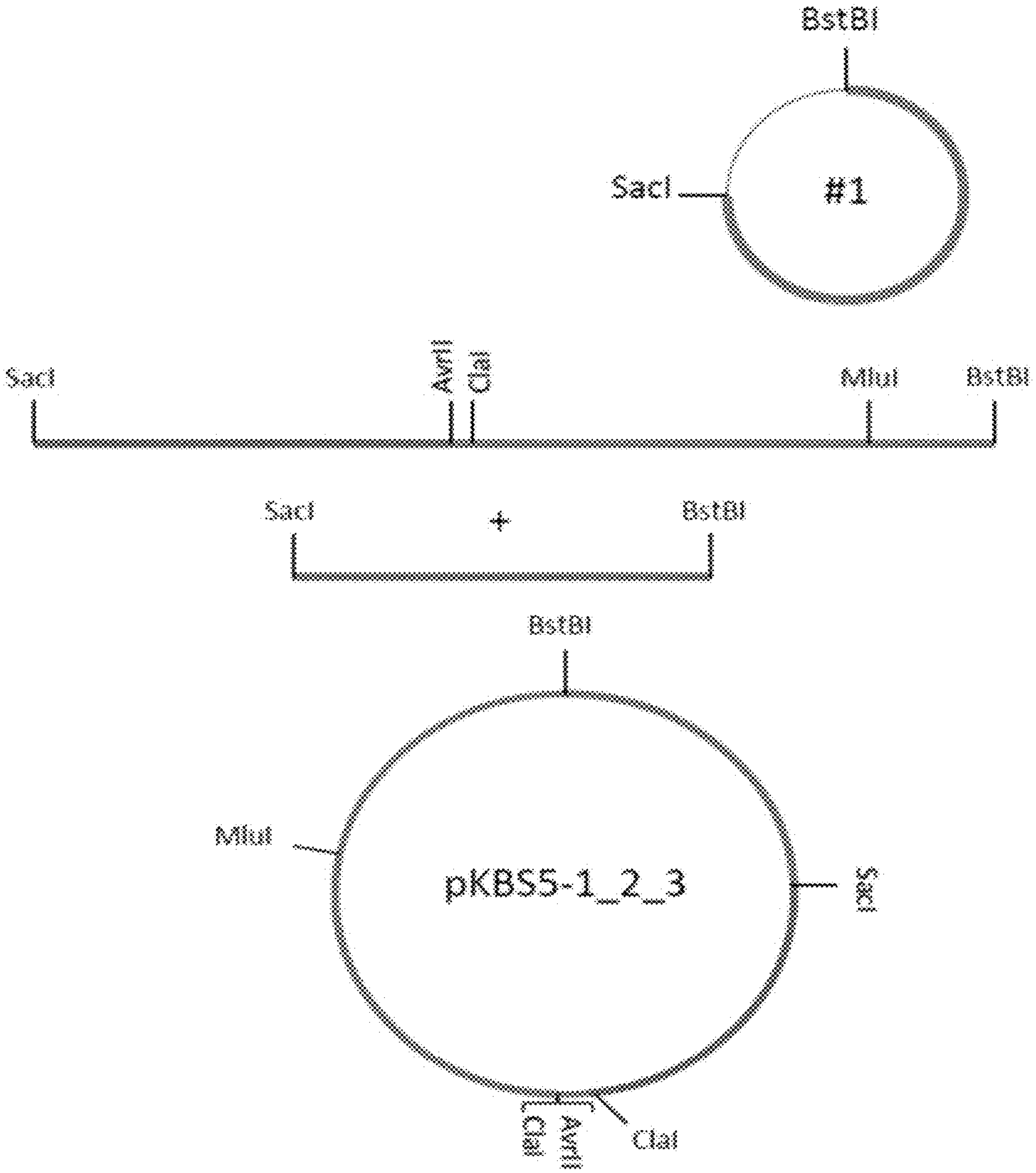
Figure 3E:
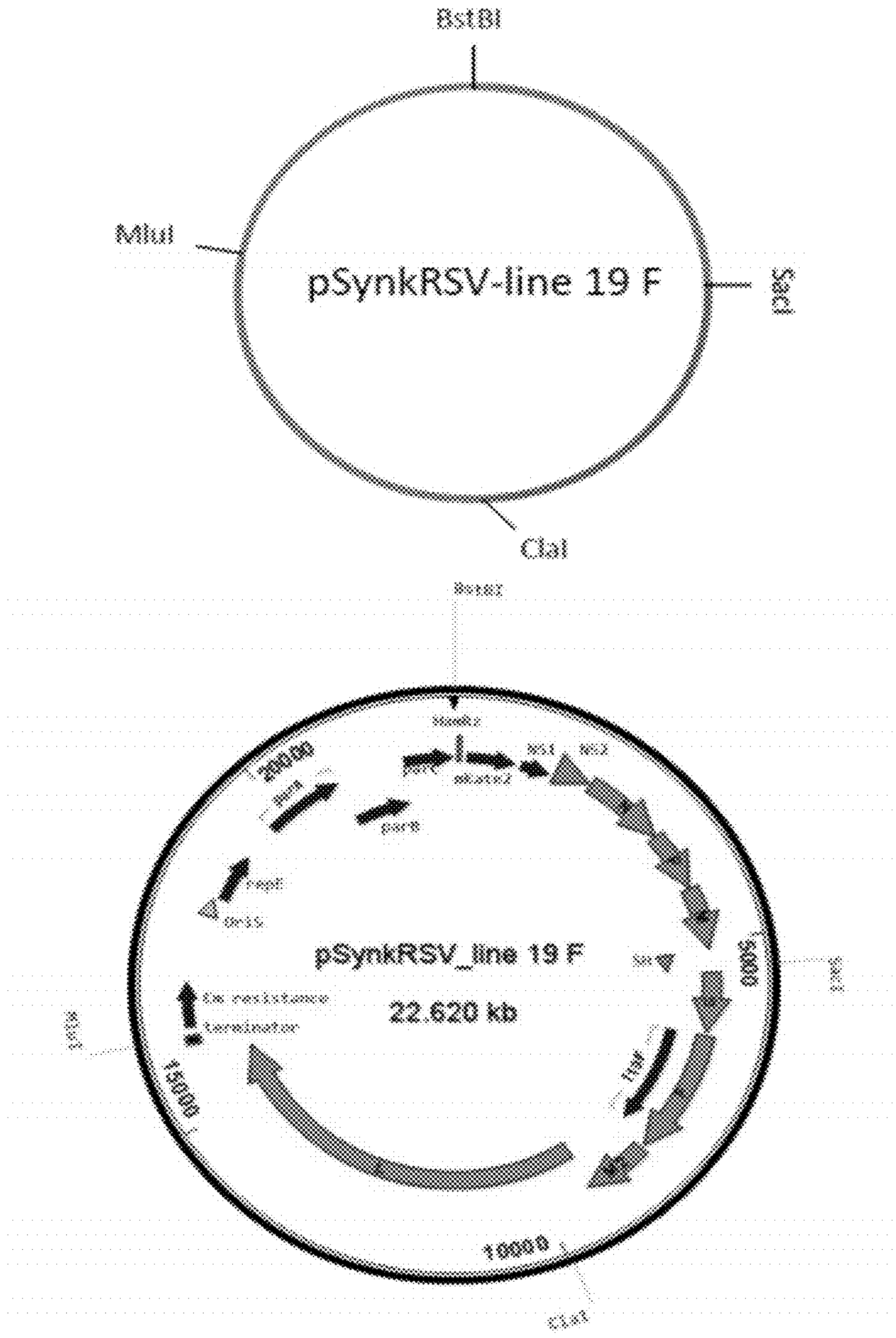

FIG. 2 shows a gel after deletion of galK operon from BAC-RSV by recombineering. MluI digest of galK-containing plasmid (lane 2), BAC mini-prep DNAs (lanes 3-7), and parental BAC-RSV clone C2 (lane 8).

FIGS. 3A-E schematically illustrate steps for creating a BAC-RSV. Three plasmids with RSV segments are generated (see experimental); A) pKBS3 is cut at BstBl and Mlul sites to linearize, and is ligated to an oligonucleotide adapter providing pKBS5; B) pSynRSV#2 with SacI and ClaI is cut and ligated to pKBS5 providing pKBS5-2; C) pSynRSV#3 with AvrII and Mlul is cut and ligated to pKBS5_2 providing pKBS5_2_3; D) pSynRSV#1 with BstB1 and SacI is cut and ligated to pKBS5_2_3 providing pKBS5_1_2_3. E). Recombineering is used to delete nucleotides between two ClaI sites generating pSynRSV-line 19F.

DETAILED DESCRIPTION

It has been discovered that cultivating RSV in *E. coli* bacteria may be accomplished by utilizing a plasmid containing a bacterial artificial chromosome. A plasmid comprising a bacterial artificial chromosome is disclosed that contains the complete antigenomic sequence of respiratory syncytial virus (RSV) strain A2 except the F gene, which is the antigenomic sequence of RSV strain line 19. Along with helper plasmids, it can be used in the reverse genetics system for the recovery of infectious virus. The antigenome sequence on the plasmid can be mutated prior to virus recovery to generate viruses with desired mutations.

The plasmid is an improvement on current RSV antigenomic plasmids for several reasons. Each RSV gene is flanked by restriction endonuclease cleavage sites to allow for easy manipulation of any gene. As a basis for viral mutagenesis, this plasmid may be used to design attenuated viruses for use in vaccines. An extra gene encoding the modified katushka, mKate2, protein has been included in the antigenome prior to the first RSV gene. Katushka is a red fluorescent protein which would be expressed in concert with the other RSV genes and would serve as visual evidence of virus replication. Changes have also been made to the ribozyme sequences that flank the RSV antigenome and play a role in the production of infectious virus through reverse genetics.

The disclosed vectors allow for efficient mutagenesis through recombineering. This mutagenesis method requires little to no ligation cloning, but relies on the recombination machinery present in bacteria harboring certain genes from a bacteriophage. Because RSV genes are often unstable in bacteria predominantly used for cloning, such as *Escherícha coli* (*E. coli*), it is believed that the single digit copy nature of the bacterial artificial chromosome avoids the trouble with instability.

Respiratory Syncytial Virus (RSV)

Typically, the RSV particle contains a viral genome within a helical nucleocapsid which is surrounded by matrix proteins and an envelope containing glycoproteins. The genome of human wild-type RSV encodes the proteins, NS1, NS2, N, P, M, SH, G, F, M2-1, M2-2, and L. G, F, and SH are glycoproteins. The F gene has been incorporated into a number of viral vaccines. RSV polymerase activity consists of the large protein (L) and phosphoprotein (P). The viral M2-1 protein is used during transcription and is likely to be a component of the transcriptase complex. The viral N protein is used to encapsidate the nascent RNA during replication.

The genome is transcribed and replicated in the cytoplasm of a host cell. Host-cell transcription typically results in synthesis of ten methylated and polyadenylated mRNAs. The antigenome is positive-sense RNA complement of the genome produced during replication, which in turn acts as a template for genome synthesis. The viral genes are flanked by conserved gene-start (GS) and gene-end (GE) sequences. At the 3' and 5' ends of the genome are leader and trailer nucleotides. The wild type leader sequence contains a promoter at the 3' end. When the viral polymerase reaches a GE signal, the polymerase polyadenylates and releases the mRNA and reinitiates RNA synthesis at the next GS signal. The L-P complex is believed to be responsible for recognition of the promoter, RNA synthesis, capping and methylation of the 5' termini of the mRNAs and polyadenylation of their 3' ends. It is believed that the polymerase sometimes dissociates from the gene at the junctions. Because the polymerase initiates transcription at the 3' end of the genome, this results in a gradient of expression, with the genes at the 3' end of the genome being transcribed more frequently than those at the 5' end.

To replicate the genome, the polymerase does not respond to the cis-acting GE and GS signals and generates positive-sense RNA complement of the genome, the antigenome. At the 3' end of the antigenome is the complement of the trailer, which contains a promoter. The polymerase uses this promoter to generate genome-sense RNA. Unlike mRNA, which is released as naked RNA, the antigenome and genome RNAs are encapsidated with virus nucleoprotein (N) as they are synthesized.

In certain embodiments, the disclosure relates to vectors and nucleic acids that contain RSV gene(s) such as the wild-type genome or antigenome. An example of an RSV antigenome is provided in U.S. Pat. No. 6,790,449, as SEQ ID NO:1 therein, hereby incorporated by reference. Reference to RSV gene(s) and the genome is contemplated to include certain mutations, deletions, or variant combinations, such as cold-passaged (cp) non-temperature sensitive (ts) derivatives of RSV, cpRSV, such as rA2 cp248/404/1030ΔSH. rA2 cp248/404ΔSH contains 4 independent attenuating genetic elements: cp which is based on 5 missense mutations in the N and L proteins and the F glycoprotein that together confer the non-ts attenuation phenotype of cpRSV; ts248, a missense mutation in the L protein; ts404, a nucleotide substitution in the gene-start transcription signal of the M2 gene; and ΔSH, complete deletion of the SH gene. rA2 cp248/404/1030ΔSH contains 5 independent attenuating genetic elements: those present in rA2 cp248/404ΔSH and ts1030, another missense mutation in the L protein. See Karron et al., J Infect Dis., 2005, 191(7): 1093-1104, hereby incorporated by reference. Within certain embodiments, it is contemplated that the RSV anitgenome may contain deletion or mutations in nonessential genes (e.g., the SH, NS1, NS2, and M2-2 genes) or combinations thereof.

It is contemplated that the nucleic acid may contain a viral genome other than RSV which includes an F gene of RSV such as live-attenuated vaccines, e.g., sendai virus (a murine parainfluenza virus) based vaccine or a live-attenuated chimeric bovine/human with human parainfluenza virus vaccine, genetically engineered to express human RSV F protein.

Bacterial Artificial Chromosomes (BACs)

In certain embodiments, the disclosure relates to vectors and nucleic acids that contain bacterial artificial chromosomes. A bacterial cloning system for mapping and analysis of complex genomes has been disclosed in Shizuya et al., Proc. Natl. Acad. Sci., 1992, 89:8794-8797. The BAC system (for bacterial artificial chromosome) is based on *Escherichia coli* and its single-copy plasmid F factor which were described as useful for cloning large fragments of human DNA. The F factor encodes for genes that regulate its own replication including oriS, repE, parA, and parB. The oriS and repE genes mediate the unidirectional replication of the F factor while parA and parB typically maintain copy number at a level of one or two per *E. coli* genome. It is contemplated that the genes and the chromosome may contain mutations, deletions, or variants with desired functional attributes. The BAC vector (pBAC) typically contains these genes as well as a resistance marker and a cloning segment containing promotors for incorporating nucleic acid segments of interest by ligating into restriction enzyme sites. Exemplary BAC systems include those described in Shizuya & Kouros-Hehr, Keio J Med, 2001, 50(1): 26-30, hereby incorporated by reference.

One may reconstitute infectious RSV virus from the RSV BAC plasmids disclosed herein. BAC vectors can be transfected to bacteria such as *E. coli* by electroporation. The RSV-BACs disclosed herein may be stably maintained in bacteria, re-isolated from the bacteria, and inserted into a eukaryotic cell along with one or more vectors that express the N, P, L, and M2-1 proteins. These cells produce infective RSV particles. Production of infectious RSV results from co-transfection of plasmids encoding N, P, L, and M2-1 proteins and the antigenome under control of the T7 promoter into BHK-21 cells that express T7 RNA polymerase (BSR cells). See Buchholz et al., J. Virol., 2000, 74(3):1187-1199, hereby incorporated by reference.

Vaccines

A number of attenuated RSV strains as candidate vaccines for intranasal administration have been developed using multiple rounds of chemical mutagenesis to introduce multiple mutations into a virus. Evaluation in rodents, chimpanzees, adults and infants indicate that certain of these candidate vaccine strains are immunogenic, and may be attenuated. Nucleotide sequence analysis of some of these attenuated viruses indicates that each level of increased attenuation is typically associated with two or more new nucleotide and amino acid substitutions.

The disclosure provides the ability to distinguish between silent incidental mutations versus those responsible for phenotype differences by introducing the mutations, separately and in various combinations, into the genome or antigenome of infectious wild-type RSV. This process identifies mutations responsible for phenotypes such as attenuation, temperature sensitivity, cold-adaptation, small plaque size, host range restriction, etc. Mutations from this menu can then be introduced in various combinations to calibrate a vaccine virus to an appropriate level of attenuation, etc., as desired. Moreover, the present disclosure provides the ability to combine mutations from different strains of virus into one strain.

The present disclosure also provides for methods of attenuation. For example, individual internal genes of human RSV can be replaced with their bovine, murine or other RSV counterpart. This may include part or all of one or more of the NS1, NS2, N, P, M, SH, M2-1, M2-2 and L genes, or parts of the G and F genes. Reciprocally, means are provided to generate a live attenuated bovine RSV by inserting human attenuating genes into a bovine RSV genome or antigenome background. Human RSV bearing bovine RSV glycoproteins provides a host range restriction favorable for human vaccine preparations. Bovine RSV sequences which can be used in the present disclosure are described in, e.g., Pastey et al., J. Gen. Viol. 76:193-197 (1993); Pastey et al., Virus Res. 29:195-202 (1993); Zamora et al., J. Gen. Virol. 73:737-741 (1992); Mallipeddi et al., J. Gen. Virol. 74:2001-2004 (1993); Mallipeddi et al., J. Gen. Virol. 73:2441-2444 (1992); and Zamora et al., Virus Res. 24:115-121 (1992), each of which is incorporated herein by reference.

The disclosure also provides the ability to analyze other types of attenuating mutation and to incorporate them into infectious RSV for vaccine or other uses. For example, a tissue culture-adapted nonpathogenic strain of pneumonia virus of mice (the murine counterpart of RSV) lacks a cytoplasmic tail of the G protein (Randhawa et al., Virology 207: 240-245 (1995)). By analogy, the cytoplasmic and transmembrane domains of each of the RSV glycoproteins, F, G and SH, can be deleted or modified to achieve attenuation.

Other mutations for use in infectious RSV of the present disclosure include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986), incorporated herein by reference) can be shortened or lengthened or changed in sequence content, and the naturally-occurring gene overlap (Collins et al., Proc. Natl. Acad. Sci. USA 84:5134-5138 (1987), incorporated herein by reference) can be removed or changed to a different intergenic region by the methods described herein.

In another embodiment, RSV useful in a vaccine formulation can be conveniently modified to accommodate antigenic drift in circulating virus. Typically the modification will be in the G and/or F proteins. The entire G or F gene, or the segment(s) encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B would broaden the response to cover a wider spectrum of the relatively diverse subgroup A and B strains present in the human population.

An infectious RSV clone of the disclosure can also be engineered to enhance its immunogenicity and induce a level of protection greater than that provided by natural infection, or vice versa, to identify and ablate epitopes associated with undesirable immunopathologic reactions. Enhanced immunogenicity of the vaccines produced by the present disclosure addresses one of the greatest obstacles to controlling RSV, namely the incomplete nature of immunity induced by natural infection. An additional gene may be inserted into or proximate to the RSV genome or antigenome which is under the control of an independent set of transcription signals. Genes of interest include those encoding cytokines (e.g., IL-2 through IL-15, especially IL-3, IL-6 and IL-7, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

Thus RSV vaccines of the disclosure contain as an active ingredient an immunogenetically effective amount of RSV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV infection, particularly of the lower respiratory tract.

The host to which the vaccine are administered can be any mammal which is susceptible to infection by RSV or a closely related virus and which host is capable of generating a protective immune response to the antigens of the vaccinizing strain. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the RSV of the disclosure are administered to a host susceptible to or otherwise at risk of RSV infection to enhance the host's own immune response capabilities. Such an amount is defined to be an "immunogenically effective dose." In this use, the precise amounts again depend on the host's state of health and weight, the mode of administration, the nature of the formulation. The vaccine formulations should provide a quantity of modified RSV of the invention sufficient to effectively protect the host patient against serious or life-threatening RSV infection.

The RSV produced in accordance with the present invention can be combined with viruses of the other subgroup or strains to achieve protection against multiple RSV subgroups or strains, or protective epitopes of these strains can be engineered into one virus as described herein. Typically the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances it may be desirable to combine the RSV vaccines of the disclosure with vaccines which induce protective responses to other agents, particularly other childhood viruses. For example, the RSV vaccine of the present disclosure can be administered simultaneously with parainfluenza virus vaccine, such as described in Clements et al., J. Clin. Microbiol. 29:1175-1182 (1991), incorporated herein by reference. In another aspect of the disclosure the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the disclosure can be carried out. In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the disclosure, the RSV is employed as a vector for transient gene therapy of the respiratory tract. According to this embodiment, the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2-1 proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

TERMS

The terms "protein" and "polypeptide" refer to compounds comprising amino acids joined via peptide bonds and are used interchangeably.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25 50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a "regulatable" or "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

Efficient expression of recombinant DNA sequences in eukaryotic cells typically requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation.

The term "vector" refers to nucleic acid molecules that transfer DNA segment(s) from one cell to another. The term "vehicle" is sometimes used interchangeably with "vector."

The terms "expression vector" or "expression cassette" refer to a recombinant nucleic acid containing a desired coding sequence and appropriate nucleic acid sequences used for the expression of the operably linked coding sequence in a particular host organism. Nucleic acid sequences used for expression in prokaryotes typically include a promoter, an operator (optional), and a ribosome binding site, often along with other sequences. Eukaryotic cells are known to utilize promoters, enhancers, and termination and polyadenylation signals.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, modified katushka, mkate and mkate2 (See, e.g., Merzlyak et al., Nat. Methods, 2007, 4, 555-557 and Shcherbo et al., Biochem. J., 2008, 418, 567-574), luciferase (See, e.g., deWet et al., Mol. Cell. Biol. 7:725 (1987) and U.S. Pat Nos., 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, beta-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" or "antigenome" refers to a nucleotide sequence whose sequence of nucleotide residues is in reverse 5' to 3' orientation in relation to the sequence of nucleotide residues in a sense strand. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex.

EXPERIMENTAL

Example 1

Expression of RSV in Plasmid Designed for Low Copy Number

Infectious recombinant RSV (rRSV) can be recovered from transfected plasmids. Co-expression of RSV N, P, L, and M2 1 proteins as well as the full-length antigenomic RNA is sufficient for RSV replication. Infectious RSV may be produced from the co-transfection of plasmids encoding N, P, L, and M2-1 proteins and the antigenome under control of the T7 promoter into BHK-21 cells that stably express T7 RNA polymerase (BSR cells). Currently research labs typically use a RSV antigenomic cDNA cloned in the plasmid pBR322 (mid-range copy number, 15-20 copies per *E coli*). In order to maintain the antigenomic cDNA in this plasmid, the bacteria is grown at 30° C. and low aeration. Nevertheless, plasmid rearrangements and clone loss is frequently experienced.

A fraction of RSV cDNA containing the attachment glycoprotein (G) and fusion (F) genes of the virus was found to be unclonable in pUC-based plasmids (500-700 plasmid copies in *E coli*). This fragment was cloned in a low copy number (approximately 5 copies per *E. coli*) plasmid called pLG338-30.5. The plasmid pLG338-30 was developed to increase the stability of cloned lentivirus glycoproteins. Cunningham et al., Gene, 1993, 124, 93-98. It is hypothesized that cDNA instability in *E coli* results from the presence of cryptic *E coli* transcription promoters within viral glycoprotein sequences. Thus, instability of cDNA in "promoterless" plasmids in bacteria can arise because aberrant proteins are expressed from cryptic promoters, leading to toxicity exacerbated by plasmid copy number.

An antigenomic plasmid was generated containing the RSV strain A2 genome with the strain line 19 F gene in place of the A2 F gene. It had been derived from the antigenome plasmid first disclosed in Collins et al., Proc Natl Acad Sci USA., 1995, 92(25):11563-11567 and U.S. Pat. No. 6,790,449 hereby incorporated by reference. The antigenome was digested out of the plasmid vector and ligated into the pKBS3 BAC.

GalK recombineering reagents were obtained from the NCI and successfully established a BAC-RSV reverse genetics protocol (FIGS. 1 and 2). See http://web.ncifcrf.gov/research/brb/recombineeringInformation.aspx, hereby incorporated by reference. Mutation of RSV cDNA via BAC recombineering has enhanced the ability to manipulate RSV for generation of mutants. An added benefit of the system is enhanced stability of the full-length antigenomic cDNA in the BAC vector.

The BAC-based RSV antigenome vector was propagated at 32° C. and 250 RPM without observing any vector rearrangements or clone loss in *E coli*. Thus, BAC-RSV not only enables manipulations via recombineering but also facilitates RSV reverse genetics in general owing to elimination of cDNA instability.

Example 2

RSV Antigenome in BAC Vector (pSynkRSV_line 19 F Construction)

The RSV-BAC pSynkRSV_line 19 F contains the modified katushka gene (mKate2, fluorescent protein), and restriction sites for more convenient cloning. To build pSynkRSV, three nucleic acid pieces were synthesized by Gene Art, a German company that synthesizes DNA. These three pieces then have to be put together in the bacterial artificial chromosome (BAC). The three pieces are designated pSynkRSV-BstBI_SacI (#1) (SEQ ID NO: 1), pSynkRSV-SacI-_ClaI (#2) (SEQ ID NO: 2), and pSynkRSV-ClaI_MluI (#3) (SEQ ID NO: 3). One uses the plasmid pKBS3 as the backbone for constructing pSynkRSV. See FIGS. 3A-E. pSynkRSV contains the bacterial artificial chromosome sequences needed to regulate copy number and partitioning in the bacteria.

To insert the three synthesized segments, one puts oligonucleotide adapters into pKBS3 between two existing restriction enzyme cut sites, BstBI and MluI.

```
                                          (SEQ ID NO: 4)
CGAATTGGGAGCTCTTTTATCGATGTTGCCTAGGTTTTA

                                          (SEQ ID NO: 5)
TTAACCCTCGAGAAAATAGCTACAACGGATCCAAAATGCGC
```

The overhangs were designed such that the adapter would ligate into pKBS3 at the BstBI and MluI sites. Underlined sequences indicate restriction sites: SacI, ClaI, and AvrII from right to left respectively. This produces a multi-cloning site containing the restriction sites BstBI, SacI, ClaI, AvrII, and MluI, in that order, and a plasmid termed pKBSS. See FIG. 3A. One cuts and ligates the SacI ClaI segment (#2) from Gene Art into pKBSS. See FIG. 3B. Next one cuts and ligates the #3 segment using the enzymes AvrII and MluI (cannot use ClaI again due to an inactive ClaI restriction site in pSynkRSV-ClaI_MluI). See FIG. 3C. At this point, the plasmid pKBSS contains the Gene Art sequences from SacI to ClaI, some intervening nucleotides (less than 10), and the Gene Art sequences from AvrII to MluI. One cuts and ligates the #1 segment using BstBI and SacI. See FIG. 3D. This RSV BAC contains about 10 unwanted nucleotides between two ClaI sites (that from segment #2 and segment #3). Recombineering is used to delete those nucleotides, thus generating pSynkRSV_line 19 F (SEQ ID NO: 6). See FIG. 3E. The three segments should be ligated in this order to avoid potential interference from multiple restriction sites.

What is claimed:

1. A vector comprising a) a bacterial artificial chromosome comprising oriS, repE, parA, and parB genes of Factor F, and b) a nucleic acid sequence comprising a respiratory syncytial virus (RSV) antigenome wherein the vector comprises restriction sites BstBI, SacI, ClaI, and MluI in that order.

2. The vector of claim 1, wherein the nucleic acid sequence comprising the RSV sequence is a strain that is optionally mutated.

3. The vector of claim 1, wherein the bacterial artificial chromosome comprises a selectable marker.

4. An isolated bacteria comprising the vector of claim 1.

5. An isolated cell comprising the vector of claim 1.

6. The isolated cell of claim 5, further comprising a vector selected from the group consisting of a vector encoding an N protein of RSV, a vector encoding a P protein of RSV, a vector encoding an L protein of RSV, and a vector encoding an M2-1 protein of RSV.

7. The isolated cell of claim 6, wherein the vector comprises a promoter and the isolated cell encodes a polypeptide that activates transcription downstream of the promoter.

8. The isolated cell of claim 7, wherein the promoter is T7.

9. The isolated cell of claim 7, wherein the polypeptide that activates transcription downstream of the promoter is T7 RNA polymerase.

10. A vector comprising a) a bacterial artificial chromosome comprising oriS, repE, parA, and parB genes of Factor F, and b) a nucleic acid sequence comprising a respiratory syncytial virus (RSV) antigenome in operable combination with a reporter gene wherein the vector comprises restriction sites BstBI, SacI, ClaI, and MluI in that order.

* * * * *

SEQUENCE LISTING

```
<160> NUMBER OF SEQ ID NOS: 6

<210> SEQ ID NO 1
<211> LENGTH: 5459
<212> TYPE: DNA
<213> ORGANISM: Artificial Sequence
<220> FEATURE:
```

-continued

<223> OTHER INFORMATION: pSynkRSV-BstBI_SacI

<400> SEQUENCE: 1

```
gggcagtgag cggaaggccc atgaggccag ttaattaaga ggtaccttcg aaacgaaatt     60
aatacgactc actataggga agtttttcgc gtctgatgag gccgttaggc cgaaactcct    120
ctccggagtc acgcgaaaaa atgcgtacaa caaacttgca taaaccaaaa aaatggggca    180
aataagaatt tgataagtac cacttaaatt taactccctt gcttagcgat ggtgagcgag    240
ctgattaagg agaacatgca catgaagctg tacatggagg gcaccgtgaa caaccaccac    300
ttcaagtgca catccgaggg cgaaggcaag ccctacgagg gcacccagac catgagaatc    360
aaggcggtcg agggcggccc tctccccttc gccttcgaca tcctggctac cagcttcatg    420
tacggcagca aaaccttcat caaccacacc cagggcatcc ccgacttctt taagcagtcc    480
ttccccgagg gcttcacatg ggagagagtc accacatacg aagacggggg cgtgctgacc    540
gctacccagg acaccagcct ccaggacggc tgcctcatct acaacgtcaa gatcagaggg    600
gtgaacttcc catccaacgg ccctgtgatg cagaagaaaa cactcggctg ggaggcctcc    660
accgagaccc tgtaccccgc tgacggcggc ctggaaggca gagccgacat ggccctgaag    720
ctcgtgggcg ggggccacct gatctgcaac ttgaagacca catacagatc caagaaaccc    780
gctaagaacc tcaagatgcc cggcgtctac tatgtggaca gaagactgga aagaatcaag    840
gaggccgaca aagagaccta cgtcgagcag cacgaggtgg ctgtggccag atactgcgac    900
ctccctagca aactggggca cagatgagta ttcaattata gttattaaaa acttaacaga    960
agacaaaaat ggggcaaata agaatttgat aagtaccact taaatttaac tcccttgctt   1020
agcgatgggc agcaattcat tgagtatgat aaaagttaga ttacaaaatt tgtttgacaa   1080
tgatgaagta gcattgttaa aaataacatg ctatactgat aaattaatac atttaactaa   1140
cgctttggct aaggcagtga tacatacaat caaattgaat ggcattgtgt ttgtgcatgt   1200
tattacaagt agtgatattt gccctaataa taatattgta gtaaaatcca atttcacaac   1260
aatgccagta ctacaaaatg gaggttatat atgggaaatg atggaattaa cacattgctc   1320
tcaacctaat ggtctactag atgacaattg tgaaattaaa ttctccaaaa aactaagtga   1380
ttcaacaatg accaattata tgaatcaatt atctgaatta cttggatttg atcttaatcc   1440
ataaattata attaatatca actagcaaat caatgtcact aacaccatta gttaatataa   1500
aacttaacag aagacaaaaa tggggcaaat aaatcaattc agccaaccca accatggaca   1560
caacccacaa tgataataca ccacaaagac tgatgatcac agacatgaga ccgttgtcac   1620
ttgagaccat aataacatca ctaaccagag acatcataac acacaaattt atatacttga   1680
taaatcatga atgcatagtg agaaaacttg atgaaagaca ggccacattt acattcctgg   1740
tcaactatga aatgaaacta ttacacaaag taggaagcac taaatataaa aaatatactg   1800
aatacaacac aaaatatggc actttcccta tgccaatatt catcaatcat gatgggttct   1860
tagaatgcat tggcattaag cctacaaagc atactcccat aatatacaag tatgatctca   1920
atccataaat ttcaacacaa tattcacaca atctaaaaca acaactctat gcataactat   1980
actccatagt ccagatggag cctgaaaatt atagtaattt aaaattaagg agagatataa   2040
gatagaagat ggggcaaata caaagatggc tcttagcaaa gtcaagttga atgatacact   2100
caacaaagat caacttctgt catccagcaa atacaccatc caacggagca caggagatag   2160
tattgatact cctaattatg atgtgcagaa acacatcaat aagttatgtg gcatgttatt   2220
aatcacagaa gatgctaatc ataaattcac tgggttaata ggtatgttat atgcgatgtc   2280
```

-continued taggttagga agagaagaca ccataaaaat actcagagat gcgggatatc atgtaaaagc 2340
aaatggagta gatgtaacaa cacatcgtca agacattaat ggaaaagaaa tgaaatttga 2400
agtgttaaca ttggcaagct taacaactga aattcaaatc aacattgaga tagaatctag 2460
aaaatcctac aaaaaaatgc taaaagaaat gggagaggta gctccagaat acaggcatga 2520
ctctcctgat tgtgggatga taatattatg tatagcagca ttagtaataa ctaaattagc 2580
agcaggggac agatctggtc ttacagccgt gattaggaga gctaataatg tcctaaaaaa 2640
tgaaatgaaa cgttacaaag gcttactacc caaggacata gccaacagct tctatgaagt 2700
gtttgaaaaa catccccact ttatagatgt ttttgttcat tttggtatag cacaatcttc 2760
taccagaggt ggcagtagag ttgaagggat ttttgcagga ttgtttatga atgcctatgg 2820
tgcagggcaa gtgatgttac ggtggggagt cttagcaaaa tcagttaaaa atattatgtt 2880
aggacatgct agtgtgcaag cagaaatgga acaagttgtt gaggtttatg aatatgccca 2940
aaaattgggt ggtgaagcag gattctacca tatattgaac aacccaaaag catcattatt 3000
atctttgact caatttcctc acttctccag tgtagtatta ggcaatgctg ctggcctagg 3060
cataatggga gagtacagag gtacaccgag gaatcaagat ctatatgatg cagcaaaggc 3120
atatgctgaa caactcaaag aaaatggtgt gattaactac agtgtactag acttgacagc 3180
agaagaacta gaggctatca aacatcagct taatccaaaa gataatgatg tagagctttg 3240
agttaataaa aaatggggca aataaatcat catggaaaag tttgctcctg aattccatgg 3300
agaagatgca aacaacaggg ctactaaatt cctagaatca ataaagggca aattcacatc 3360
acccaaagat cccaagaaaa aagatagtat catatctgtc aactcaatag atatagaagt 3420
aaccaaagaa agccctataa catcaaattc aactattatc aacccaacaa atgagacaga 3480
tgatactgca gggaacaagc ccaattatca aagaaaacct ctagtaagtt tcaaagaaga 3540
ccctacacca agtgataatc ccttttctaa actatacaaa gaaaccatag aaacatttga 3600
taacaatgaa gaagaatcca gctattcata cgaagaaata aatgatcaga caaacgataa 3660
tataacagca agattagata ggattgatga aaaattaagt gaaatactag gaatgcttca 3720
cacattagta gtggcaagtg caggacctac atctgctcgg gatggtataa gagatgccat 3780
gattggttta agagaagaaa tgatagaaaa aatcagaact gaagcattaa tgaccaatga 3840
cagattagaa gctatggcaa gactcaggaa tgaggaaagt gaaaagatgg caaaagacac 3900
atcagatgaa gtgtctctca atccaacatc agagaaattg aacaacctat tggaagggaa 3960
tgatagtgac aatgatctat cacttgaaga tttctgatta gttaccactc ttcacatcaa 4020
cacacaatac caacagaaga ccaacaaact aaccaaccca atcatccaac caaacatcca 4080
tccgccaatc agccaaacag ccaacaaaac aaccagccaa tccaaaacta accacccgga 4140
aaaaatctat aatatagtta caaaaaaagg aaagggtggg gcaaatatgg aaacatacgt 4200
gaacaagctt cacgaaggct ccacatacac agctgctgtt caatacaatg tcttagaaaa 4260
agacgatgac cctgcatcac ttacaatatg ggtgcccatg ttccaatcat ctatgccagc 4320
agatttactt ataaaagaac tagctaatgt caacatacta gtgaaacaaa tatccacacc 4380
caagggacct tcactaagag tcatgataaa ctcaagaagt gcagtgctag cacaaatgcc 4440
cagcaaattt accatatgcg ctaatgtgtc cttggatgaa agaagcaaac tagcatatga 4500
tgtaaccaca ccctgtgaaa tcaaggcatg tagtctaaca tgcctaaaat caaaaaatat 4560
gttgactaca gttaaagatc tcactatgaa gacactcaac cctacacatg atattattgc 4620

-continued

```
tttatgtgaa tttgaaaaca tagtaacatc aaaaaaagtc ataataccaa catacctaag   4680

atccatcagt gtcagaaata aagatctgaa cacacttgaa aatataacaa ccactgaatt   4740

caaaaatgct atcacaaatg caaaaatcat cccttactca ggattactat tagtcatcac   4800

agtgactgac aacaaaggag cattcaaata cataaagcca caaagtcaat tcatagtaga   4860

tcttggagct tacctagaaa aagaaagtat atattatgtt accacaaatt ggaagcacac   4920

agctacacga tttgcaatca aacccatgga agattaacct ttttcctcta catcagtgtg   4980

ttaattcata caaactttct acctacattc ttcacttcac catcacaatc acaaacactc   5040

tgtggttcaa ccaatcaaac aaaacttatc tgaagtccca gatcatccca agtcattgtt   5100

tatcagatct agtactcaaa taagttaata aaaaatatac acatggacgt ccatggggca   5160

aataatcatt ggaggaaatc caactaatca caatatctgt taacatagac aagtccacac   5220

accatacaga atcaaccaat ggaaaataca tccataacaa tagaattctc aagcaaattc   5280

tggccttact ttacactaat acacatgatc acaacaataa tctctttgct aatcataatc   5340

tccatcatga ttgcaatact aaacaaactt tgtgaatata acgtattcca taacaaaacc   5400

tttgagttac caagagctca tggcgcgcct aggccttgac ggccttccgc caattcgcc    5459
```

<210> SEQ ID NO 2
<211> LENGTH: 4523
<212> TYPE: DNA
<213> ORGANISM: Artificial Sequence
<220> FEATURE:
<223> OTHER INFORMATION: pSynkRSV-SacI_ClaI

<400> SEQUENCE: 2

```
ttagggccca acaatgaact aggatatcaa gactaacaat aacattgggg caaatgcaaa     60

catgtccaaa aacaaggacc aacgcaccgc taagacatta gaaaggacct gggacactct    120

caatcattta ttattcatat catcgtgctt atataagtta aatcttaaat ctgtagcaca    180

aatcacatta tccattctgg caatgataat ctcaacttca cttataattg cagccatcat    240

attcatagcc tcggcaaacc acaaagtcac accaacaact gcaatcatac aagatgcaac    300

aagccagatc aagaacacaa ccccaacata cctcacccag aatcctcagc ttggaatcag    360

tccctctaat ccgtctgaaa ttacatcaca aatcaccacc atactagctt caacaacacc    420

aggagtcaag tcaaccctgc aatccacaac agtcaagacc aaaaacacaa caacaactca    480

aacacaaccc agcaagccca ccacaaaaca acgccaaaac aaaccaccaa gcaaacccaa    540

taatgatttt cactttgaag tgttcaactt tgtaccctgc agcatatgca gcaacaatcc    600

aacctgctgg gctatctgca aaagaatacc aaacaaaaaa ccaggaaaga aaaccactac    660

caagcccaca aaaaaaccaa ccctcaagac aaccaaaaaa gatcccaaac ctcaaaccac    720

taaatcaaag gaagtaccca ccaccaagcc cacagaagag ccaaccatca acaccaccaa    780

aacaaacatc ataactacac tactcacctc caacaccaca ggaaatccag aactcacaag    840

tcaaatggaa accttccact caacttcctc cgaaggcaat ccaagccctt ctcaagtctc    900

tacaacatcc gagtacccat cacaaccttc atctccaccc aacacaccac gccagtagtt    960

acttaaaaac atattatcac aaaaggcctt gaccaaccgc ggagaatcaa aataaactct   1020

ggggcaaata acaatggagt tgccaatcct caaagcaaat gcaattacca caatcctcgc   1080

tgcagtcaca ttttgctttg cttctagtca aaacatcact gaagaatttt atcaatcaac   1140

atgcagtgca gttagcaaag gctatcttag tgctctaaga actggttggt atactagtgt   1200

tataactata gaattaagta atatcaagaa aaataagtgt aatggaacag atgctaaggt   1260
```

-continued

```
aaaattgatg aaacaagaat tagataaata taaaaatgct gtaacagaat tgcagttgct   1320
catgcaaagc acaccagcag caaacaatcg agccagaaga gaactaccaa ggtttatgaa   1380
ttatacactc aacaatacca aaaaaaccaa tgtaacatta agcaagaaaa ggaaaagaag   1440
atttcttggt tttttgttag gtgttggatc tgcaatcgcc agtggcattg ctgtatctaa   1500
ggtcctgcac ttagaaggag aagtgaacaa gatcaaaagt gctctactat ccacaaacaa   1560
ggccgtagtc agcttatcaa atggagttag tgtcttaacc agcagagtgt tagacctcaa   1620
aaactatata gataaacaat tgttacctat tgtgaataag caaagctgca gaatatcaaa   1680
tatagaaact gtgatagagt tccaacaaaa gaacaacaga ctactagaga ttaccaggga   1740
atttagtgtt aatgcaggtg taactacacc tgtaagcact tacatgttaa ctaatagtga   1800
attattgtca ttaatcaatg atatgcctat aacaaatgat cagaaaaagt taatgtccaa   1860
caatgttcaa atagttagac agcaaagtta ctctatcatg tccataataa aagaggaagt   1920
cttagcatat gtagtacaat taccactata tggtgtgata gatacacctt gttggaaatt   1980
acacacatcc cctctatgta caaccaacac aaaagaaggg tcaaacatct gtttaacaag   2040
aactgacaga ggatggtact gtgacaatgc aggatcagta tctttcttcc cacaagctga   2100
aaaatgtaaa gttcaatcga atcgagtatt ttgtgacaca atgtacagtt taacattacc   2160
aagtgaagta aatctctgca atgttgacat attcaatccc aaatatgatt gtaaaattat   2220
gacttcaaaa acagatgtaa gcagctccgt tatcacatct ctaggagcca ttgtgtcatg   2280
ctatggcaaa actaaatgta cagcatccaa taaaaatcgt ggaatcataa agacattttc   2340
taacgggtgt gattatgtat caaataaagg ggtggacact gtgtctgtag gtaacacatt   2400
atattatgta aataagcaag aaggcaaaag tctctatgta aaaggtgaac caataataaa   2460
tttctatgac ccattagtat tcccctctga tgaatttgat gcatcaatat ctcaagtcaa   2520
tgagaagatt aaccagagtt tagcatttat tcgtaaatcc gatgaattat tacataatgt   2580
aaatgctggt aaatcaacca caaatatcat gataactact ataattatag tgattatagt   2640
aatattgtta tcattaattg ctgttggact gctcctatac tgtaaggcca gaagcacacc   2700
aatcacacta agcaaggatc aactgagtgg tataaataat attgcattta gtaactgaat   2760
aaaaatagca cctaatcatg ttcttacaat ggtttactat ctgctcatag acaacccatc   2820
tatcattgga ttttcttaaa atctgaactt catcgaaact cttatctata aaccatctca   2880
cttacactat ttaagtagat tcctagttta tagttatata aaacacaatt gaatgccagt   2940
cgaccttacc atctgtaaaa atgaaaactg gggcaaatat gtcacgaagg aatccttgca   3000
aatttgaaat tcgaggtcat tgcttaaatg gtaagaggtg tcattttagt cataattatt   3060
ttgaatggcc accccatgca ctgcttgtaa gacaaaactt tatgttaaac agaatactta   3120
agtctatgga taaaagtata gataccttat cagaaataag tggagctgca gagttggaca   3180
gaacagaaga gtatgctctt ggtgtagttg gagtgctaga gagttatata ggatcaataa   3240
acaatataac taaacaatca gcatgtgttg ccatgagcaa actcctcact gaactcaata   3300
gtgatgatat caaaaagctg agggacaatg aagagctaaa ttcacccaag ataagagtgt   3360
acaatactgt catatcatat attgaaagca acaggaaaaa caataaacaa actatccatc   3420
tgttaaaaag attgccagca gacgtattga agaaaaccat caaaaacaca ttggatatcc   3480
ataagagcat aaccatcaac aacccaaaag aatcaactgt tagtgataca aatgaccatg   3540
ccaaaaataa tgatactacc tgacaaatat ccttgtagta taacttccat actaataaca   3600
```

```
agtagatgta gagttactat gtataatcaa aagaacacac tatatttcaa tcaaaacaac   3660

ccaaataacc atatgtactc accgaatcaa acattcaatg aaatccattg gacctctcaa   3720

gaattgattg acacaattca aaattttcta caacatctag gtattattga ggatatatat   3780

acaatatata tattagtgtc ataacactca attctaacac tcaccacatc gttacattat   3840

taattcaaac aattcaagtt gtgggacaaa atggatccca ttattaatgg aaattctgct   3900

aatgtttatc taaccgatag ttatttaaaa ggtgttatct ctttctcaga gtgtaatgct   3960

ttaggaagtt acatattcaa tggtccttat ctcaaaaatg attataccaa cttaattagt   4020

agacaaaatc cattaataga acacatgaat ctaaagaaac taaatataac acagtcctta   4080

atatctaagt atcataaagg tgaaataaaa ttagaagaac ctacttattt tcagtcatta   4140

cttatgacat acaagagtat gacctcgtca gaacagattg ctaccactaa tttacttaaa   4200

aagataataa gaagagctat agaaataagt gatgtcaaag tctatgctat attgaataaa   4260

ctagggctta aagaaaagga caagattaaa tccaacaatg gacaagatga agacaactca   4320

gttattacga ccataatcaa agatgatata ctttcagctg taatcaaaac aacactcttg   4380

aagaaattga tgtgttcaat gcaacatcct ccatcatggt taatacattg gtttaactta   4440

tacacaaaat taaacaacat attaacacag tatcgatggt acctcttaat taactggcct   4500

catgggcctt ccgctcactg ccc                                           4523
```

<210> SEQ ID NO 3
<211> LENGTH: 6369
<212> TYPE: DNA
<213> ORGANISM: Artificial Sequence
<220> FEATURE:
<223> OTHER INFORMATION: pSynkRSV-ClaI_MluI

<400> SEQUENCE: 3

```
ggcgaattgg cggaaggccg tcaaggccta ggcgcgccat gagctcatcg atcaaatgag     60

gtaaaaaacc atgggtttac attgatagat aatcaaactc ttagtggatt tcaatttatt    120

ttgaaccaat atggttgtat agtttatcat aaggaactca aaagaattac tgtgacaacc    180

tataatcaat tcttgacatg gaaagatatt agccttagta gattaaatgt ttgtttaatt    240

acatggatta gtaactgctt gaacacatta aataaaagct taggcttaag atgcggattc    300

aataatgtta tcttgacaca actattcctt tatggagatt gtatactaaa gctatttcac    360

aatgaggggt tctacataat aaaagaggta gagggattta ttatgtctct aattttaaat    420

ataacagaag aagatcaatt cagaaaacga ttttataata gtatgctcaa caacatcaca    480

gatgctgcta ataaagctca gaaaaatctg ctatcaagag tatgtcatac attattagat    540

aagacagtgt ccgataatat aataaatggc agatggataa ttctattaag taagttcctt    600

aaattaatta agcttgcagg tgacaataac cttaacaatc tgagtgaact atatttttg     660

ttcagaatat ttggacaccc aatggtagat gaaagacaag ccatggatgc tgttaaaatt    720

aattgcaatg agaccaaatt ttacttgtta agcagtctga gtatgttaag aggtgccttt    780

atatatagaa ttataaaagg gtttgtaaat aattacaaca gatggcctac tttaagaaat    840

gctattgttt taccttaag atggttaact tactataaac taaacactta tccttctttg     900

ttggaactta cagaaagaga tttgattgtg ttatcaggac tacgtttcta tcgtgagttt    960

cggttgccta aaaaagtgga tcttgaaatg attataaatg ataaagctat atcacctcct   1020

aaaaatttga tatggactag tttccctaga aattacatgc catcacacat acaaaactat   1080

atagaacatg aaaaattaaa attttccgag agtgataaat caagaagagt attagagtat   1140
```

-continued

```
tatttaagag ataacaaatt caatgaatgt gatttataca actgtgtagt taatcaaagt   1200
tatctcaaca accctaatca tgtggtatca ttgacaggca aagaaagaga actcagtgta   1260
ggtagaatgt ttgcaatgca accgggaatg ttcagacagg ttcaaatatt ggcagagaaa   1320
atgatagctg aaaacatttt acaattcttt cctgaaagtc ttacaagata tggtgatcta   1380
gaactacaaa aaatattaga attgaaagca ggaataagta acaaatcaaa tcgctacaat   1440
gataattaca acaattacat tagtaagtgc tctatcatca cagatctcag caaattcaat   1500
caagcatttc gatatgaaac gtcatgtatt tgtagtgatg tgctggatga actgcatggt   1560
gtacaatctc tattttcctg gttacattta actattcctc atgtcacaat aatatgcaca   1620
tataggcatg cacccccta tataggagat catattgtag atcttaacaa tgtagatgaa   1680
caaagtggat tatatagata tcacatgggt ggcatcgaag ggtggtgtca aaaactgtgg   1740
accatagaag ctatatcact attggatcta atatctctca aagggaaatt ctcaattact   1800
gctttaatta atggtgacaa tcaatcaata gatataagca aaccaatcag actcatggaa   1860
ggtcaaactc atgctcaagc agattatttg ctagcattaa atagccttaa attactgtat   1920
aaagagtatg caggcatagg ccacaaatta aaaggaactg agacttatat atcacgagat   1980
atgcaattta tgagtaaaac aattcaacat aacggtgtat attacccagc tagtataaag   2040
aaagtcctaa gagtgggacc gtggataaac actatacttg atgatttcaa agtgagtcta   2100
gaatctatag gtagtttgac acaagaatta gaatatagag gtgaaagtct attatgcagt   2160
ttaatattta gaaatgtatg gttatataat cagattgctc tacaattaaa aaatcatgca   2220
ttatgtaaca ataaactata tttggacata ttaaaggttc tgaaacactt aaaaaccttt   2280
tttaatcttg ataatattga tacagcatta acattgtata tgaatttacc catgttattt   2340
ggtggtggtg atcccaactt gttatatcga agtttctata gaagaactcc tgacttcctc   2400
acagaggcta tagttcactc tgtgttcata cttagttatt atacaaacca tgacttaaaa   2460
gataaacttc aagatctgtc agatgataga ttgaataagt tcttaacatg cataatcacg   2520
tttgacaaaa accctaatgc tgaattcgta acattgatga gagatcctca agctttaggg   2580
tctgagagac aagctaaaat tactagcgaa atcaatagac tggcagttac agaggttttg   2640
agtacagctc caaacaaaat attctccaaa agtgcacaac attatactac tacagagata   2700
gatctaaatg atattatgca aaatatagaa cctacatatc ctcatgggct aagagttgtt   2760
tatgaaagtt taccctttta taaagcagag aaaatagtaa atcttatatc aggtacaaaa   2820
tctataacta acatactgga aaaaacttct gccatagact taacagatat tgatagagcc   2880
actgagatga tgaggaaaaa cataactttg cttataagga tacttccatt ggattgtaac   2940
agagataaaa gagagatatt gagtatggaa aacctaagta ttactgaatt aagcaaatat   3000
gttagggaaa gatcttggtc tttatccaat atagttggtg ttacatcacc cagtatcatg   3060
tatacaatgg acatcaaata tactacaagc actatatcta gtggcataat tatagagaaa   3120
tataatgtta acagtttaac acgtggtgag agaggaccca ctaaaccatg ggttggttca   3180
tctacacaag agaaaaaaac aatgccagtt tataatagac aagtcttaac caaaaaacag   3240
agagatcaaa tagatctatt agcaaaattg gattgggtgt atgcatctat agataacaag   3300
gatgaattca tggaagaact cagcatagga acccttgggt taacatatga aaaggccaag   3360
aaattatttc cacaatattt aagtgtcaat tatttgcatc gccttacagt cagtagtaga   3420
ccatgtgaat tccctgcatc aataccagct tatagaacaa caaattatca ctttgacact   3480
```

-continued

```
agccctatta atcgcatatt aacagaaaag tatggtgatg aagatattga catagtattc   3540
caaaactgta taagctttgg ccttagttta atgtcagtag tagaacaatt tactaatgta   3600
tgtcctaaca gaattattct catacctaag cttaatgaga tacatttgat gaaacctccc   3660
atattcacag gtgatgttga tattcacaag ttaaaacaag tgatacaaaa acagcatatg   3720
tttttaccag acaaaataag tttgactcaa tatgtggaat tattcttaag taataaaaca   3780
ctcaaatctg gatctcatgt taattctaat ttaatattgg cacataaaat atctgactat   3840
tttcataata cttacatttt aagtactaat ttagctggac attggattct gattatacaa   3900
cttatgaaag attctaaagg tatttttgaa aaagattggg gagagggata tataactgat   3960
catatgttta ttaatttgaa agttttcttc aatgcttata agacctatct cttgtgtttt   4020
cataaaggtt atggcaaagc aaagctggag tgtgatatga acacttcaga tcttctatgt   4080
gtattggaat taatagacag tagttattgg aagtctatgt ctaaggtatt tttagaacaa   4140
aaagttatca aatacattct tagccaagat gcaagtttac atagagtaaa aggatgtcat   4200
agcttcaaat tatggtttct taaacgtctt aatgtagcag aattcacagt ttgcccttgg   4260
gttgttaaca tagattatca tccaacacat atgaaagcaa tattaactta tatagatctt   4320
gttagaatgg gattgataaa tatagataga atacacatta aaaataaaca caaattcaat   4380
gatgaatttt atacttctaa tctcttctac attaattata acttctcaga taatactcat   4440
ctattaacta aacatataag gattgctaat tctgaattag aaaataatta caacaaatta   4500
tatcatccta caccagaaac cctagagaat atactagcca atccgattaa aagtaatgac   4560
aaaaagacac tgaatgacta ttgtataggt aaaaatgttg actcaataat gttaccattg   4620
ttatctaata agaagcttat taaatcgtct gcaatgatta gaaccaatta cagcaaacaa   4680
gatttgtata atttattccc tatggttgtg attgatagaa ttatagatca ttcaggcaat   4740
acagccaaat ccaaccaact ttacactact acttcccacc aaatatcttt agtgcacaat   4800
agcacatcac tttactgcat gcttccttgg catcatatta atagattcaa ttttgtattt   4860
agttctacag gttgtaaaat tagtatagag tatattttaa aagatcttaa aattaaagat   4920
cccaattgta tagcattcat aggtgaagga gcagggaatt tattattgcg tacagtagtg   4980
gaacttcatc ctgacataag atatatttac agaagtctga aagattgcaa tgatcatagt   5040
ttacctattg agtttttaag gctgtacaat ggacatatca acattgatta tggtgaaaat   5100
ttgaccattc ctgctacaga tgcaaccaac aacattcatt ggtcttattt acatataaag   5160
tttgctgaac ctatcagtct tttgtctgt gatgccgaat tgtctgtaac agtcaactgg    5220
agtaaaatta taatagaatg gagcaagcat gtaagaaagt gcaagtactg ttcctcagtt   5280
aataaatgta tgttaatagt aaaatatcat gctcaagatg atattgattt caaattagac   5340
aatataacta tattaaaaac ttatgtatgc ttaggcagta agttaaaggg atcggaggtt   5400
tacttagtcc ttacaatagg tcctgcgaat atattcccag tatttaatgt agtacaaaat   5460
gctaaattga tactatcaag aaccaaaaat ttcatcatgc ctaagaaagc tgataaagag   5520
tctattgatg caaatattaa aagtttgata ccctttcttt gttaccctat aacaaaaaaa   5580
ggaattaata ctgcattgtc aaaactaaag agtgttgtta gtggagatat actatcatat   5640
tctatagctg gacgtaatga agttttcagc aataaactta taaatcataa gcatatgaac   5700
atcttaaaat ggttcaatca tgttttaaat ttcagatcaa cagaactaaa ctataaccat   5760
ttatatatgg tagaatctac atatccttac ctaagtgaat tgttaaacag cttgacaacc   5820
aatgaactta aaaaactgat taaaatcaca ggtagtctgt tatacaactt tcataatgaa   5880
```

-continued

```
taatgaataa agatcttata ataaaaattc ccatagctat acactaacac tgtattcaat   5940

tatagttatt aaaaattaaa aatcgtacga ttttttaaat aacttttagt gaactaatcc   6000

taaagttatc attttaatct tggaggaata aatttaaacc ctaatctaat tggtttatat   6060

gtgtattaac taaattacga gatattagtt tttgacactt tttttctcgt gggtcggcat   6120

ggcatctcca cctcctcgcg gtccgacctg ggcatccgaa ggaggacgca cgtccactcg   6180

gatggctaag ggagctgcta acaaagcccg aaaggaagct gagttggctg ctgccaccgc   6240

tgagcaataa ctagcataac cccttggggc ctctaaacgg gtcttgaggg gttttttgct   6300

gaaaggagga actatatacg cgtggtacct cttaattaac tggcctcatg ggccttccgc   6360

tcactgccc                                                            6369
```

<210> SEQ ID NO 4
<211> LENGTH: 39
<212> TYPE: DNA
<213> ORGANISM: Artificial Sequence
<220> FEATURE:
<223> OTHER INFORMATION: BstBI

<400> SEQUENCE: 4

```
cgaattggga gctcttttat cgatgttgcc taggtttta                            39
```

<210> SEQ ID NO 5
<211> LENGTH: 41
<212> TYPE: DNA
<213> ORGANISM: Artificial Sequence
<220> FEATURE:
<223> OTHER INFORMATION: MluI

<400> SEQUENCE: 5

```
ttaaccctcg agaaaatagc tacaacggat ccaaaatgcg c                          41
```

<210> SEQ ID NO 6
<211> LENGTH: 22620
<212> TYPE: DNA
<213> ORGANISM: Artificial Sequence
<220> FEATURE:
<223> OTHER INFORMATION: pSynkRSVl19F

<400> SEQUENCE: 6

```
aaacggatcc ttcgaaacga aattaatacg actcactata gggaagtttt tcgcgtctga     60

tgaggccgtt aggccgaaac tcctctccgg agtcacgcga aaaaatgcgt acaacaaact    120

tgcataaacc aaaaaaatgg ggcaaataag aatttgataa gtaccactta aatttaactc    180

ccttgcttag cgatggtgag cgagctgatt aaggagaaca tgcacatgaa gctgtacatg    240

gagggcaccg tgaacaacca ccacttcaag tgcacatccg agggcgaagg caagccctac    300

gagggcaccc agaccatgag aatcaaggcg gtcgagggcg gccctctccc cttcgccttc    360

gacatcctgg ctaccagctt catgtacggc agcaaaacct tcatcaacca cacccagggc    420

atccccgact tctttaagca gtccttcccc gagggcttca catgggagag agtcaccaca    480

tacgaagacg ggggcgtgct gaccgctacc caggacacca gcctccagga cggctgcctc    540

atctacaacg tcaagatcag aggggtgaac ttcccatcca acggccctgt gatgcagaag    600

aaaacactcg gctgggaggc ctccaccgag accctgtacc ccgctgacgg cggcctggaa    660

ggcagagccg acatggccct gaagctcgtg ggcgggggcc acctgatctg caacttgaag    720

accacataca gatccaagaa acccgctaag aacctcaaga tgcccggcgt ctactatgtg    780
```

-continued

```
gacagaagac tggaaagaat caaggaggcc gacaaagaga cctacgtcga gcagcacgag    840
gtggctgtgg ccagatactg cgacctccct agcaaactgg ggcacagatg agtattcaat    900
tatagttatt aaaaacttaa cagaagacaa aaatggggca aataagaatt tgataagtac    960
cacttaaatt taactccctt gcttagcgat gggcagcaat tcattgagta tgataaaagt   1020
tagattacaa aatttgtttg acaatgatga agtagcattg ttaaaaataa catgctatac   1080
tgataaatta atacatttaa ctaacgcttt ggctaaggca gtgatacata caatcaaatt   1140
gaatggcatt gtgtttgtgc atgttattac aagtagtgat atttgcccta ataataatat   1200
tgtagtaaaa tccaatttca caacaatgcc agtactacaa aatggaggtt atatatggga   1260
aatgatggaa ttaacacatt gctctcaacc taatggtcta ctagatgaca attgtgaaat   1320
taaattctcc aaaaaactaa gtgattcaac aatgaccaat tatatgaatc aattatctga   1380
attacttgga tttgatctta atccataaat tataattaat atcaactagc aaatcaatgt   1440
cactaacacc attagttaat ataaaactta acagaagaca aaaatggggc aaataaatca   1500
attcagccaa cccaaccatg gacacaaccc acaatgataa tacaccacaa agactgatga   1560
tcacagacat gagaccgttg tcacttgaga ccataataac atcactaacc agagacatca   1620
taacacacaa atttatatac ttgataaatc atgaatgcat agtgagaaaa cttgatgaaa   1680
gacaggccac atttacattc ctggtcaact atgaaatgaa actattacac aaagtaggaa   1740
gcactaaata taaaaaatat actgaataca acacaaaata tggcactttc cctatgccaa   1800
tattcatcaa tcatgatggg ttcttagaat gcattggcat taagcctaca aagcatactc   1860
ccataatata caagtatgat ctcaatccat aaatttcaac acaatattca cacaatctaa   1920
aacaacaact ctatgcataa ctatactcca tagtccagat ggagcctgaa aattatagta   1980
atttaaaatt aaggagagat ataagataga agatggggca aatacaaaga tggctcttag   2040
caaagtcaag ttgaatgata cactcaacaa agatcaactt ctgtcatcca gcaaatacac   2100
catccaacgg agcacaggag atagtattga tactcctaat tatgatgtgc agaaacacat   2160
caataagtta tgtggcatgt tattaatcac agaagatgct aatcataaat tcactgggtt   2220
aataggtatg ttatatgcga tgtctaggtt aggaagagaa gacaccataa aaatactcag   2280
agatgcggga tatcatgtaa aagcaaatgg agtagatgta acaacacatc gtcaagacat   2340
taatggaaaa gaaatgaaat ttgaagtgtt aacattggca agcttaacaa ctgaaattca   2400
aatcaacatt gagatagaat ctagaaaatc ctacaaaaaa atgctaaaag aaatgggaga   2460
ggtagctcca gaatacaggc atgactctcc tgattgtggg atgataatat tatgtatagc   2520
agcattagta ataactaaat tagcagcagg ggacagatct ggtcttacag ccgtgattag   2580
gagagctaat aatgtcctaa aaaatgaaat gaaacgttac aaaggcttac tacccaagga   2640
catagccaac agcttctatg aagtgtttga aaaacatccc cactttatag atgtttttgt   2700
tcattttggt atagcacaat cttctaccag aggtggcagt agagttgaag ggatttttgc   2760
aggattgttt atgaatgcct atggtgcagg gcaagtgatg ttacggtggg gagtcttagc   2820
aaaatcagtt aaaaatatta tgttaggaca tgctagtgtg caagcagaaa tggaacaagt   2880
tgttgaggtt tatgaatatg cccaaaaatt gggtggtgaa gcaggattct accatatatt   2940
gaacaaccca aaagcatcat tattatcttt gactcaattt cctcacttct ccagtgtagt   3000
attaggcaat gctgctggcc taggcataat gggagagtac agaggtacac cgaggaatca   3060
agatctatat gatgcagcaa aggcatatgc tgaacaactc aaagaaaatg gtgtgattaa   3120
ctacagtgta ctagacttga cagcagaaga actagaggct atcaaacatc agcttaatcc   3180
```

-continued

```
aaaagataat gatgtagagc tttgagttaa taaaaaatgg ggcaaataaa tcatcatgga   3240
aaagtttgct cctgaattcc atggagaaga tgcaaacaac agggctacta aattcctaga   3300
atcaataaag ggcaaattca catcacccaa agatcccaag aaaaaagata gtatcatatc   3360
tgtcaactca atagatatag aagtaaccaa agaaagccct ataacatcaa attcaactat   3420
tatcaaccca acaaatgaga cagatgatac tgcagggaac aagcccaatt atcaaagaaa   3480
acctctagta agtttcaaag aagaccctac accaagtgat aatccctttt ctaaactata   3540
caaagaaacc atagaaacat ttgataacaa tgaagaagaa tccagctatt catacgaaga   3600
aataaatgat cagacaaacg ataatataac agcaagatta gataggattg atgaaaaatt   3660
aagtgaaata ctaggaatgc ttcacacatt agtagtggca agtgcaggac ctacatctgc   3720
tcgggatggt ataagagatg ccatgattgg tttaagagaa gaaatgatag aaaaaatcag   3780
aactgaagca ttaatgacca atgacagatt agaagctatg gcaagactca ggaatgagga   3840
aagtgaaaag atggcaaaag acacatcaga tgaagtgtct ctcaatccaa catcagagaa   3900
attgaacaac ctattggaag ggaatgatag tgacaatgat ctatcacttg aagatttctg   3960
attagttacc actcttcaca tcaacacaca ataccaacag aagaccaaca aactaaccaa   4020
cccaatcatc caaccaaaca tccatccgcc aatcagccaa acagccaaca aaacaaccag   4080
ccaatccaaa actaaccacc cggaaaaaat ctataatata gttacaaaaa aaggaaaggg   4140
tggggcaaat atggaaacat acgtgaacaa gcttcacgaa ggctccacat acacagctgc   4200
tgttcaatac aatgtcttag aaaaagacga tgaccctgca tcacttacaa tatgggtgcc   4260
catgttccaa tcatctatgc cagcagattt acttataaaa gaactagcta atgtcaacat   4320
actagtgaaa caaatatcca cacccaaggg accttcacta agagtcatga taaactcaag   4380
aagtgcagtg ctagcacaaa tgcccagcaa atttaccata tgcgctaatg tgtccttgga   4440
tgaaagaagc aaactagcat atgatgtaac cacaccctgt gaaatcaagg catgtagtct   4500
aacatgccta aaatcaaaaa atatgttgac tacagttaaa gatctcacta tgaagacact   4560
caaccctaca catgatatta ttgctttatg tgaatttgaa aacatagtaa catcaaaaaa   4620
agtcataata ccaacatacc taagatccat cagtgtcaga aataaagatc tgaacacact   4680
tgaaaatata acaaccactg aattcaaaaa tgctatcaca aatgcaaaaa tcatccctta   4740
ctcaggatta ctattagtca tcacagtgac tgacaacaaa ggagcattca aatacataaa   4800
gccacaaagt caattcatag tagatcttgg agcttaccta gaaaaagaaa gtatatatta   4860
tgttaccaca aattggaagc acacagctac acgatttgca atcaaaccca tggaagatta   4920
accttttttcc tctacatcag tgtgttaatt catacaaact ttctacctac attcttcact   4980
tcaccatcac aatcacaaac actctgtggt tcaaccaatc aaacaaaact tatctgaagt   5040
cccagatcat cccaagtcat tgtttatcag atctagtact caaataagtt aataaaaaat   5100
atacacatgg acgtccatgg ggcaaataat cattggagga aatccaacta atcacaatat   5160
ctgttaacat agacaagtcc acacaccata cagaatcaac caatggaaaa tacatccata   5220
acaatagaat tctcaagcaa attctggcct tactttacac taatacacat gatcacaaca   5280
ataatctctt tgctaatcat aatctccatc atgattgcaa tactaaacaa actttgtgaa   5340
tataacgtat tccataacaa aacctttgag ttaccaagag ctcgagttaa tacttgataa   5400
agtagttaat taaaaattag ggcccaacaa tgaactagga tatcaagact aacaataaca   5460
ttggggcaaa tgcaaacatg tccaaaaaca aggaccaacg caccgctaag acattagaaa   5520
```

-continued

```
ggacctggga cactctcaat catttattat tcatatcatc gtgcttatat aagttaaatc   5580
ttaaatctgt agcacaaatc acattatcca ttctggcaat gataatctca acttcactta   5640
taattgcagc catcatattc atagcctcgg caaaccacaa agtcacacca acaactgcaa   5700
tcatacaaga tgcaacaagc cagatcaaga acacaacccc aacatacctc acccagaatc   5760
ctcagcttgg aatcagtccc tctaatccgt ctgaaattac atcacaaatc accaccatac   5820
tagcttcaac aacaccagga gtcaagtcaa ccctgcaatc cacaacagtc aagaccaaaa   5880
acacaacaac aactcaaaca caacccagca agcccaccac aaaacaacgc caaaacaaac   5940
caccaagcaa acccaataat gattttcact ttgaagtgtt caactttgta ccctgcagca   6000
tatgcagcaa caatccaacc tgctgggcta tctgcaaaag aataccaaac aaaaaaccag   6060
gaaagaaaac cactaccaag cccacaaaaa aaccaaccct caagacaacc aaaaaagatc   6120
ccaaacctca aaccactaaa tcaaaggaag tacccaccac caagcccaca gaagagccaa   6180
ccatcaacac caccaaaaca aacatcataa ctacactact cacctccaac accacaggaa   6240
atccagaact cacaagtcaa atggaaacct tccactcaac ttcctccgaa ggcaatccaa   6300
gcccttctca agtctctaca acatccgagt acccatcaca accttcatct ccacccaaca   6360
caccacgcca gtagttactt aaaaacatat tatcacaaaa ggccttgacc aaccgcggag   6420
aatcaaaata aactctgggg caaataacaa tggagttgcc aatcctcaaa gcaaatgcaa   6480
ttaccacaat cctcgctgca gtcacatttt gctttgcttc tagtcaaaac atcactgaag   6540
aattttatca atcaacatgc agtgcagtta gcaaaggcta tcttagtgct ctaagaactg   6600
gttggtatac tagtgttata actatagaat taagtaatat caagaaaaat aagtgtaatg   6660
gaacagatgc taaggtaaaa ttgatgaaac aagaattaga taaatataaa aatgctgtaa   6720
cagaattgca gttgctcatg caaagcacac cagcagcaaa caatcgagcc agaagagaac   6780
taccaaggtt tatgaattat acactcaaca ataccaaaaa aaccaatgta acattaagca   6840
agaaaaggaa aagaagattt cttggttttt tgttaggtgt tggatctgca atcgccagtg   6900
gcattgctgt atctaaggtc ctgcacttag aaggagaagt gaacaagatc aaaagtgctc   6960
tactatccac aaacaaggcc gtagtcagct tatcaaatgg agttagtgtc ttaaccagca   7020
gagtgttaga cctcaaaaac tatatagata aacaattgtt acctattgtg aataagcaaa   7080
gctgcagaat atcaaatata gaaactgtga tagagttcca acaaaagaac aacagactac   7140
tagagattac cagggaattt agtgttaatg caggtgtaac tacacctgta agcacttaca   7200
tgttaactaa tagtgaatta ttgtcattaa tcaatgatat gcctataaca aatgatcaga   7260
aaaagttaat gtccaacaat gttcaaatag ttagacagca aagttactct atcatgtcca   7320
taataaaaga ggaagtctta gcatatgtag tacaattacc actatatggt gtgatagata   7380
caccttgttg gaaattacac acatcccctc tatgtacaac caacacaaaa gaagggtcaa   7440
acatctgttt aacaagaact gacagaggat ggtactgtga caatgcagga tcagtatctt   7500
tcttcccaca agctgaaaaa tgtaaagttc aatcgaatcg agtattttgt gacacaatgt   7560
acagtttaac attaccaagt gaagtaaatc tctgcaatgt tgacatattc aatcccaaat   7620
atgattgtaa aattatgact tcaaaaacag atgtaagcag ctccgttatc acatctctag   7680
gagccattgt gtcatgctat ggcaaaacta aatgtacagc atccaataaa aatcgtggaa   7740
tcataaagac attttctaac gggtgtgatt atgtatcaaa taaaggggtg gacactgtgt   7800
ctgtaggtaa cacattatat tatgtaaata agcaagaagg caaaagtctc tatgtaaaag   7860
gtgaaccaat aataaatttc tatgacccat tagtattccc ctctgatgaa tttgatgcat   7920
```

-continued

```
caatatctca agtcaatgag aagattaacc agagtttagc atttattcgt aaatccgatg   7980

aattattaca taatgtaaat gctggtaaat caaccacaaa tatcatgata actactataa   8040

ttatagtgat tatagtaata ttgttatcat taattgctgt tggactgctc ctatactgta   8100

aggccagaag cacaccaatc acactaagca aggatcaact gagtggtata aataatattg   8160

catttagtaa ctgaataaaa atagcaccta atcatgttct tacaatggtt tactatctgc   8220

tcatagacaa cccatctatc attggatttt cttaaaatct gaacttcatc gaaactctta   8280

tctataaacc atctcactta cactatttaa gtagattcct agtttatagt tatataaaac   8340

acaattgaat gccagtcgac cttaccatct gtaaaaatga aaactggggc aaatatgtca   8400

cgaaggaatc cttgcaaatt tgaaattcga ggtcattgct taaatggtaa gaggtgtcat   8460

tttagtcata attattttga atggccaccc catgcactgc ttgtaagaca aaactttatg   8520

ttaaacagaa tacttaagtc tatggataaa agtatagata ccttatcaga aataagtgga   8580

gctgcagagt tggacagaac agaagagtat gctcttggtg tagttggagt gctagagagt   8640

tatataggat caataaacaa tataactaaa caatcagcat gtgttgccat gagcaaactc   8700

ctcactgaac tcaatagtga tgatatcaaa aagctgaggg acaatgaaga gctaaattca   8760

cccaagataa gagtgtacaa tactgtcata tcatatattg aaagcaacag gaaaaacaat   8820

aaacaaacta tccatctgtt aaaaagattg ccagcagacg tattgaagaa aaccatcaaa   8880

aacacattgg atatccataa gagcataacc atcaacaacc caaaagaatc aactgttagt   8940

gatacaaatg accatgccaa aaataatgat actacctgac aaatatcctt gtagtataac   9000

ttccatacta ataacaagta gatgtagagt tactatgtat aatcaaaaga acacactata   9060

tttcaatcaa aacaacccaa ataaccatat gtactcaccg aatcaaacat tcaatgaaat   9120

ccattggacc tctcaagaat tgattgacac aattcaaaat tttctacaac atctaggtat   9180

tattgaggat atatatacaa tatatatatt agtgtcataa cactcaattc taacactcac   9240

cacatcgtta cattattaat tcaaacaatt caagttgtgg gacaaaatgg atcccattat   9300

taatggaaat tctgctaatg tttatctaac cgatagttat ttaaaaggtg ttatctcttt   9360

ctcagagtgt aatgctttag gaagttacat attcaatggt ccttatctca aaaatgatta   9420

taccaactta attagtagac aaaatccatt aatagaacac atgaatctaa agaaactaaa   9480

tataacacag tccttaatat ctaagtatca taaaggtgaa ataaaattag aagaacctac   9540

ttattttcag tcattactta tgacatacaa gagtatgacc tcgtcagaac agattgctac   9600

cactaattta cttaaaaaga taataagaag agctatagaa ataagtgatg tcaaagtcta   9660

tgctatattg aataaactag ggcttaaaga aaaggacaag attaaatcca acaatggaca   9720

agatgaagac aactcagtta ttacgaccat aatcaaagat gatatacttt cagctgttaa   9780

agataatcaa tctcatctta aagcagacaa aaatcactct acaaaacaaa aagacacaat   9840

caaaacaaca ctcttgaaga aattgatgtg ttcaatgcaa catcctccat catggttaat   9900

acattggttt aacttataca caaaattaaa caacatatta acacagtatc gatcaaatga   9960

ggtaaaaaac catgggttta cattgataga taatcaaact cttagtggat ttcaatttat  10020

tttgaaccaa tatggttgta tagtttatca taaggaactc aaaagaatta ctgtgacaac  10080

ctataatcaa ttcttgacat ggaaagatat tagccttagt agattaaatg tttgtttaat  10140

tacatggatt agtaactgct tgaacacatt aaataaaagc ttaggcttaa gatgcggatt  10200

caataatgtt atcttgacac aactattcct ttatggagat tgtatactaa agctatttca  10260
```

-continued caatgagggg ttctacataa taaaagaggt agagggattt attatgtctc taattttaaa 10320
tataacagaa gaagatcaat tcagaaaacg attttataat agtatgctca acaacatcac 10380
agatgctgct aataaagctc agaaaaatct gctatcaaga gtatgtcata cattattaga 10440
taagacagtg tccgataata taataaatgg cagatggata attctattaa gtaagttcct 10500
taaattaatt aagcttgcag gtgacaataa ccttaacaat ctgagtgaac tatatttttt 10560
gttcagaata tttggacacc caatggtaga tgaaagacaa gccatggatg ctgttaaaat 10620
taattgcaat gagaccaaat tttacttgtt aagcagtctg agtatgttaa gaggtgcctt 10680
tatatataga attataaaag ggtttgtaaa taattacaac agatggccta ctttaagaaa 10740
tgctattgtt ttacccttaa gatggttaac ttactataaa ctaaacactt atccttcttt 10800
gttggaactt acagaaagag atttgattgt gttatcagga ctacgtttct atcgtgagtt 10860
tcggttgcct aaaaaagtgg atcttgaaat gattataaat gataaagcta tatcacctcc 10920
taaaaatttg atatggacta gtttccctag aaattacatg ccatcacaca tacaaaacta 10980
tatagaacat gaaaaattaa aattttccga gagtgataaa tcaagaagag tattagagta 11040
ttatttaaga gataacaaat tcaatgaatg tgatttatac aactgtgtag ttaatcaaag 11100
ttatctcaac aaccctaatc atgtggtatc attgacaggc aaagaaagag aactcagtgt 11160
aggtagaatg tttgcaatgc aaccgggaat gttcagacag gttcaaatat tggcagagaa 11220
aatgatagct gaaaacattt tacaattctt tcctgaaagt cttacaagat atggtgatct 11280
agaactacaa aaaatattag aattgaaagc aggaataagt aacaaatcaa atcgctacaa 11340
tgataattac aacaattaca ttagtaagtg ctctatcatc acagatctca gcaaattcaa 11400
tcaagcattt cgatatgaaa cgtcatgtat ttgtagtgat gtgctggatg aactgcatgg 11460
tgtacaatct ctattttcct ggttacattt aactattcct catgtcacaa taatatgcac 11520
atataggcat gcacccccct atataggaga tcatattgta gatcttaaca atgtagatga 11580
acaaagtgga ttatatagat atcacatggg tggcatcgaa gggtggtgtc aaaaactgtg 11640
gaccatagaa gctatatcac tattggatct aatatctctc aaagggaaat tctcaattac 11700
tgctttaatt aatggtgaca atcaatcaat agatataagc aaaccaatca gactcatgga 11760
aggtcaaact catgctcaag cagattattt gctagcatta aatagcctta aattactgta 11820
taaagagtat gcaggcatag gccacaaatt aaaaggaact gagacttata tatcacgaga 11880
tatgcaattt atgagtaaaa caattcaaca taacggtgta tattacccag ctagtataaa 11940
gaaagtccta agagtgggac cgtggataaa cactatactt gatgatttca aagtgagtct 12000
agaatctata ggtagtttga cacaagaatt agaatataga ggtgaaagtc tattatgcag 12060
tttaatattt agaaatgtat ggttatataa tcagattgct ctacaattaa aaaatcatgc 12120
attatgtaac aataaactat atttggacat attaaaggtt ctgaaacact taaaaacctt 12180
ttttaatctt gataatattg atacagcatt aacattgtat atgaatttac ccatgttatt 12240
tggtggtggt gatcccaact tgttatatcg aagtttctat agaagaactc ctgacttcct 12300
cacagaggct atagttcact ctgtgttcat acttagttat tatacaaacc atgacttaaa 12360
agataaactt caagatctgt cagatgatag attgaataag ttcttaacat gcataatcac 12420
gtttgacaaa aaccctaatg ctgaattcgt aacattgatg agagatcctc aagctttagg 12480
gtctgagaga caagctaaaa ttactagcga aatcaataga ctggcagtta cagaggtttt 12540
gagtacagct ccaaacaaaa tattctccaa aagtgcacaa cattatacta ctacagagat 12600
agatctaaat gatattatgc aaaatataga acctacatat cctcatgggc taagagttgt 12660

-continued ttatgaaagt ttacccttt ataaagcaga gaaaatagta aatcttatat caggtacaaa 12720
atctataact aacatactgg aaaaaacttc tgccatagac ttaacagata ttgatagagc 12780
cactgagatg atgaggaaaa acataacttt gcttataagg atacttccat tggattgtaa 12840
cagagataaa agagagatat tgagtatgga aaacctaagt attactgaat taagcaaata 12900
tgttagggaa agatcttggt ctttatccaa tatagttggt gttacatcac ccagtatcat 12960
gtatacaatg gacatcaaat atactacaag cactatatct agtggcataa ttatagagaa 13020
atataatgtt aacagtttaa cacgtggtga gagaggaccc actaaaccat gggttggttc 13080
atctacacaa gagaaaaaaa caatgccagt ttataataga caagtcttaa ccaaaaaaca 13140
gagagatcaa atagatctat tagcaaaatt ggattgggtg tatgcatcta tagataacaa 13200
ggatgaattc atggaagaac tcagcatagg aacccttggg ttaacatatg aaaaggccaa 13260
gaaattattt ccacaatatt taagtgtcaa ttatttgcat cgccttacag tcagtagtag 13320
accatgtgaa ttccctgcat caataccagc ttatagaaca acaaattatc actttgacac 13380
tagccctatt aatcgcatat taacagaaaa gtatggtgat gaagatattg acatagtatt 13440
ccaaaactgt ataagctttg gccttagttt aatgtcagta gtagaacaat ttactaatgt 13500
atgtcctaac agaattattc tcatacctaa gcttaatgag atacatttga tgaaacctcc 13560
catattcaca ggtgatgttg atattcacaa gttaaaacaa gtgatacaaa aacagcatat 13620
gtttttacca gacaaaataa gtttgactca atatgtggaa ttattcttaa gtaataaaac 13680
actcaaatct ggatctcatg ttaattctaa tttaatattg gcacataaaa tatctgacta 13740
ttttcataat acttacattt taagtactaa tttagctgga cattggattc tgattataca 13800
acttatgaaa gattctaaag gtatttttga aaaagattgg ggagagggat atataactga 13860
tcatatgttt attaatttga aagttttctt caatgcttat aagacctatc tcttgtgttt 13920
tcataaaggt tatggcaaag caaagctgga gtgtgatatg aacacttcag atcttctatg 13980
tgtattggaa ttaatagaca gtagttattg gaagtctatg tctaaggtat tttagaaca 14040 aaaagttatc aaatacattc ttagccaaga tgcaagttta catagagtaa aaggatgtca 14100
tagcttcaaa ttatggtttc ttaaacgtct taatgtagca gaattcacag tttgcccttg 14160
ggttgttaac atagattatc atccaacaca tatgaaagca atattaactt atatagatct 14220
tgttagaatg ggattgataa atatagatag aatacacatt aaaaataaac acaaattcaa 14280
tgatgaattt tatacttcta atctcttcta cattaattat aacttctcag ataatactca 14340
tctattaact aaacatataa ggattgctaa ttctgaatta gaaaataatt acaacaaatt 14400
atatcatcct acaccagaaa ccctagagaa tatactagcc aatccgatta aaagtaatga 14460
caaaaagaca ctgaatgact attgtatagg taaaaatgtt gactcaataa tgttaccatt 14520
gttatctaat aagaagctta ttaaatcgtc tgcaatgatt agaaccaatt acagcaaaca 14580
agatttgtat aatttattcc ctatggttgt gattgataga attatagatc attcaggcaa 14640
tacagccaaa tccaaccaac tttacactac tacttcccac caaatatctt tagtgcacaa 14700
tagcacatca ctttactgca tgcttccttg gcatcatatt aatagattca attttgtatt 14760
tagttctaca ggttgtaaaa ttagtataga gtatatttta aaagatctta aaattaaaga 14820
tcccaattgt atagcattca taggtgaagg agcagggaat ttattattgc gtacagtagt 14880
ggaacttcat cctgacataa gatatattta cagaagtctg aaagattgca atgatcatag 14940
tttacctatt gagtttttaa ggctgtacaa tggacatatc aacattgatt atggtgaaaa 15000

-continued

```
tttgaccatt cctgctacag atgcaaccaa caacattcat tggtcttatt tacatataaa  15060
gtttgctgaa cctatcagtc tttttgtctg tgatgccgaa ttgtctgtaa cagtcaactg  15120
gagtaaaatt ataatagaat ggagcaagca tgtaagaaag tgcaagtact gttcctcagt  15180
taataaatgt atgttaatag taaaatatca tgctcaagat gatattgatt tcaaattaga  15240
caatataact atattaaaaa cttatgtatg cttaggcagt aagttaaagg gatcggaggt  15300
ttacttagtc cttacaatag gtcctgcgaa tatattccca gtatttaatg tagtacaaaa  15360
tgctaaattg atactatcaa gaaccaaaaa tttcatcatg cctaagaaag ctgataaaga  15420
gtctattgat gcaaatatta aaagtttgat accctttctt tgttacccta taacaaaaaa  15480
aggaattaat actgcattgt caaaactaaa gagtgttgtt agtggagata tactatcata  15540
ttctatagct ggacgtaatg aagttttcag caataaactt ataaatcata agcatatgaa  15600
catcttaaaa tggttcaatc atgttttaaa tttcagatca acagaactaa actataacca  15660
tttatatatg gtagaatcta catatcctta cctaagtgaa ttgttaaaca gcttgacaac  15720
caatgaactt aaaaaactga ttaaaatcac aggtagtctg ttatacaact ttcataatga  15780
ataatgaata aagatcttat aataaaaatt cccatagcta tacactaaca ctgtattcaa  15840
ttatagttat taaaaattaa aaatcgtacg atttttaaa taacttttag tgaactaatc  15900
ctaaagttat cattttaatc ttggaggaat aaatttaaac cctaatctaa ttggtttata  15960
tgtgtattaa ctaaattacg agatattagt ttttgacact ttttttctcg tgggtcggca  16020
tggcatctcc acctcctcgc ggtccgacct gggcatccga aggaggacgc acgtccactc  16080
ggatggctaa gggagctgct aacaaagccc gaaaggaagc tgagttggct gctgccaccg  16140
ctgagcaata actagcataa ccccttgggg cctctaaacg ggtcttgagg ggtttttttgc  16200
tgaaaggagg aactatatac gcgtaagctt ctcgacccat tctcatgttt gacagcttat  16260
catcgaattt ctgccattca tccgcttatt atcacttatt caggcgtagc aaccaggcgt  16320
ttaagggcac caataactgc cttaaaaaaa ttacgccccg ccctgccact catcgcagta  16380
ctgttgtaat tcattaagca ttctgccgac atggaagcca tcacagacgg catgatgaac  16440
ctgaatcgcc agcggcatca gcaccttgtc gccttgcgta taatatttgc ccatggtgaa  16500
aacgggggcg aagaagttgt ccatattggc cacgtttaaa tcaaaactgg tgaaactcac  16560
ccagggattg gctgagacga aaaacatatt ctcaataaac cctttaggga aataggccag  16620
gttttcaccg taacacgcca catcttgcga atatatgtgt agaaactgcc ggaaatcgtc  16680
gtggtattca ctccagagcg atgaaaacgt ttcagtttgc tcatggaaaa cggtgtaaca  16740
agggtgaaca ctatcccata tcaccagctc accgtctttc attgccatac ggaattccgg  16800
atgagcattc atcaggcggg caagaatgtg aataaaggcc ggataaaact tgtgcttatt  16860
tttctttacg gtctttaaaa aggccgtaat atccagctga acggtctggt tataggtaca  16920
ttgagcaact gactgaaatg cctcaaaatg ttctttacga tgccattggg atatatcaac  16980
ggtggtatat ccagtgattt ttttctccat tttagcttcc ttagctcctg aaaatctcga  17040
taactcaaaa aatacgcccg gtagtgatct tatttcatta tggtgaaagt tggaacctct  17100
tacgtgccga tcaacgtctc attttcgcca aaagttggcc cagggcttcc cggtatcaac  17160
agggacacca ggatttattt attctgcgaa gtgatcttcc gtcacaggta tttattcgcg  17220
ataagctcat ggagcggcgt aaccgtcgca caggaaggac agagaaagcg cggatctggg  17280
aagtgacgga cagaacggtc aggacctgga ttggggaggc ggttgccgcc gctgctgctg  17340
acggtgtgac gttctctgtt ccggtcacac cacatacgtt ccgccattcc tatgcgatgc  17400
```

acatgctgta tgccggtata ccgctgaaag ttctgcaaag cctgatggga cataagtcca 17460
tcagttcaac ggaagtctac acgaaggttt ttgcgctgga tgtggctgcc cggcaccggg 17520
tgcagtttgc gatgccggag tctgatgcgg ttgcgatgct gaaacaatta tcctgagaat 17580
aaatgccttg gcctttatat ggaaatgtgg aactgagtgg atatgctgtt tttgtctgtt 17640
aaacagagaa gctggctgtt atccactgag aagcgaacga aacagtcggg aaaatctccc 17700
attatcgtag agatccgcat tattaatctc aggagcctgt gtagcgttta taggaagtag 17760
tgttctgtca tgatgcctgc aagcggtaac gaaaacgatt tgaatatgcc ttcaggaaca 17820
atagaaatct tcgtgcggtg ttacgttgaa gtggagcgga ttatgtcagc aatggacaga 17880
acaacctaat gaacacagaa ccatgatgtg gtctgtcctt ttacagccag taggctcgcc 17940
gcagtcgagc gacggcgaag ccctcgagtg agcgaggaag caccagggaa cagcacttat 18000
atattctgct tacacacgat gcctgaaaaa acttcccttg gggttatcca cttatccacg 18060
gggatatttt tataattatt ttttttatag tttttagatc ttctttttta gagcgccttg 18120
taggccttta tccatgctgg ttctagagaa ggtgttgtga caaattgccc tttcagtgtg 18180
acaaatcacc ctcaaatgac agtcctgtct gtgacaaatt gcccttaacc ctgtgacaaa 18240
ttgccctcag aagaagctgt tttttcacaa agttatccct gcttattgac tctttttttat 18300
ttagtgtgac aatctaaaaa cttgtcacac ttcacatgga tctgtcatgg cggaaacagc 18360
ggttatcaat cacaagaaac gtaaaaatag cccgcgaatc gtccagtcaa acgacctcac 18420
tgaggcggca tatagtctct cccgggatca aaaacgtatg ctgtatctgt tcgttgacca 18480
gatcagaaaa tctgatggca ccctacagga acatgacggt atctgcgaga tccatgttgc 18540
taaatatgct gaaatattcg gattgacctc tgcggaagcc agtaaggata tacggcaggc 18600
attgaagagt ttcgcgggga aggaagtggt tttttatcgc cctgaagagg atgccggcga 18660
tgaaaaaggc tatgaatctt ttccttggtt tatcaaacgt gcgcacagtc catccagagg 18720
gctttacagt gtacatatca acccatatct cattcccttc tttatcgggt tacagaaccg 18780
gtttacgcag tttcggctta gtgaaacaaa agaaatcacc aatccgtatg ccatgcgttt 18840
atacgaatcc ctgtgtcagt atcgtaagcc ggatggctca ggcatcgtct ctctgaaaat 18900
cgactggatc atagagcgtt accagctgcc tcaaagttac cagcgtatgc ctgacttccg 18960
ccgccgcttc ctgcaggtct gtgttaatga gatcaacagc agaactccaa tgcgcctctc 19020
atacattgag aaaaagaaag gccgccagac gactcatatc gtattttcct tccgcgatat 19080
cacttccatg acgacaggat agtctgaggg ttatctgtca cagatttgag ggtggttcgt 19140
cacatttgtt ctgacctact gagggtaatt tgtcacagtt ttgctgtttc cttcagcctg 19200
catggatttt ctcatacttt ttgaactgta atttttaagg aagccaaatt tgagggcagt 19260
ttgtcacagt tgatttcctt ctctttccct tcgtcatgtg acctgatatc ggggggttagt 19320
tcgtcatcat tgatgagggt tgattatcac agtttattac tctgaattgg ctatccgcgt 19380
gtgtacctct acctggagtt tttcccacgg tggatatttc ttcttgcgct gagcgtaaga 19440
gctatctgac agaacagttc ttctttgctt cctcgccagt tcgctcgcta tgctcggtta 19500
cacggctgcg gcgagcgcta gtgataataa gtgactgagg tatgtgctct tcttatctcc 19560
ttttgtagtg ttgctcttat tttaaacaac tttgcggttt tttgatgact ttgcgatttt 19620
gttgttgctt tgcagtaaat tgcaagattt aataaaaaaa cgcaaagcaa tgattaaagg 19680
atgttcagaa tgaaactcat ggaaacactt aaccagtgca taaacgctgg tcatgaaatg 19740

```
acgaaggcta tcgccattgc acagtttaat gatgacagcc cggaagcgag gaaaataacc  19800
cggcgctgga gaataggtga agcagcggat ttagttgggg tttcttctca ggctatcaga  19860
gatgccgaga aagcagggcg actaccgcac ccggatatgg aaattcgagg acgggttgag  19920
caacgtgttg gttatacaat tgaacaaatt aatcatatgc gtgatgtgtt tggtacgcga  19980
ttgcgacgtg ctgaagacgt atttccaccg gtgatcgggg ttgctgccca taaaggtggc  20040
gtttacaaaa cctcagtttc tgttcatctt gctcaggatc tggctctgaa ggggctacgt  20100
gttttgctcg tggaaggtaa cgacccccag ggaacagcct caatgtatca cggatgggta  20160
ccagatcttc atattcatgc agaagacact ctcctgcctt tctatcttgg ggaaaaggac  20220
gatgtcactt atgcaataaa gcccacttgc tggccggggc ttgacattat tccttcctgt  20280
ctggctctgc accgtattga aactgagtta atgggcaaat ttgatgaagg taaactgccc  20340
accgatccac acctgatgct ccgactggcc attgaaactg ttgctcatga ctatgatgtc  20400
atagttattg acagcgcgcc taacctgggt atcggcacga ttaatgtcgt atgtgctgct  20460
gatgtgctga ttgttcccac gcctgctgag ttgtttgact acacctccgc actgcagttt  20520
ttcgatatgc ttcgtgatct gctcaagaac gttgatctta aagggttcga gcctgatgta  20580
cgtattttgc ttaccaaata cagcaatagt aatggctctc agtccccgtg gatggaggag  20640
caaattcggg atgcctgggg aagcatggtt ctaaaaaatg ttgtacgtga aacggatgaa  20700
gttggtaaag gtcagatccg gatgagaact gtttttgaac aggccattga tcaacgctct  20760
tcaactggtg cctggagaaa tgctctttct atttgggaac ctgtctgcaa tgaaattttc  20820
gatcgtctga ttaaaccacg ctgggagatt agataatgaa gcgtgcgcct gttattccaa  20880
aacatacgct caatactcaa ccggttgaag atacttcgtt atcgacacca gctgccccga  20940
tggtggattc gttaattgcg cgcgtaggag taatggctcg cggtaatgcc attactttgc  21000
ctgtatgtgg tcgggatgtg aagtttactc ttgaagtgct ccggggtgat agtgttgaga  21060
agacctctcg ggtatggtca ggtaatgaac gtgaccagga gctgcttact gaggacgcac  21120
tggatgatct catcccttct tttctactga ctggtcaaca gacaccggcg ttcggtcgaa  21180
gagtatctgg tgtcatagaa attgccgatg ggagtcgccg tcgtaaagct gctgcactta  21240
ccgaaagtga ttatcgtgtt ctggttggcg agctggatga tgagcagatg gctgcattat  21300
ccagattggg taacgattat cgcccaacaa gtgcttatga acgtggtcag cgttatgcaa  21360
gccgattgca gaatgaattt gctggaaata tttctgcgct ggctgatgcg gaaaatattt  21420
cacgtaagat tattacccgc tgtatcaaca ccgccaaatt gcctaaatca gttgttgctc  21480
ttttttctca ccccggtgaa ctatctgccc ggtcaggtga tgcacttcaa aaagccttta  21540
cagataaaga ggaattactt aagcagcagg catctaacct tcatgagcag aaaaaagctg  21600
gggtgatatt tgaagctgaa gaagttatca ctcttttaac ttctgtgctt aaaacgtcat  21660
ctgcatcaag aactagttta agctcacgac atcagtttgc tcctggagcg acagtattgt  21720
ataagggcga taaaatggtg cttaacctgg acaggtctcg tgttccaact gagtgtatag  21780
agaaaattga ggccattctt aaggaacttg aaaagccagc accctgatgc gaccacgttt  21840
tagtctacgt ttatctgtct ttacttaatg tcctttgtta caggccagaa agcataactg  21900
gcctgaatat tctctctggg cccactgttc cacttgtatc gtcggtctga taatcagact  21960
gggaccacgg tcccactcgt atcgtcggtc tgattattag tctgggacca cggtcccact  22020
cgtatcgtcg gtctgattat tagtctggga ccacggtccc actcgtatcg tcggtctgat  22080
aatcagactg ggaccacggt cccactcgta tcgtcggtct gattattagt ctgggaccat  22140
```

-continued

```
ggtcccactc gtatcgtcgg tctgattatt agtctgggac cacggtccca ctcgtatcgt  22200
cggtctgatt attagtctgg aaccacggtc ccactcgtat cgtcggtctg attattagtc  22260
tgggaccacg gtcccactcg tatcgtcggt ctgattatta gtctgggacc acgatcccac  22320
tcgtgttgtc ggtctgatta tcggtctggg accacggtcc cacttgtatt gtcgatcaga  22380
ctatcagcgt gagactacga ttccatcaat gcctgtcaag ggcaagtatt gacatgtcgt  22440
cgtaacctgt agaacggagt aacctcggtg tgcggttgta tgcctgctgt ggattgctgc  22500
tgtgtcctgc ttatccacaa cattttgcgc acggttatgt ggacaaaata cctggttacc  22560
caggccgtgc cggcacgtta accgggctgc atccgatgca agtgtgtcgc tgtcgagttt  22620
```